US008703947B2

(12) United States Patent
Ghosh

(10) Patent No.: US 8,703,947 B2
(45) Date of Patent: Apr. 22, 2014

(54) COMPOUNDS FOR TREATMENT OF ALZHEIMER'S DISEASE

(75) Inventor: Arun K. Ghosh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/123,157

(22) PCT Filed: Oct. 9, 2009

(86) PCT No.: PCT/US2009/060132
§ 371 (c)(1),
(2), (4) Date: Apr. 7, 2011

(87) PCT Pub. No.: WO2010/042796
PCT Pub. Date: Apr. 15, 2010

(65) Prior Publication Data
US 2011/0195978 A1    Aug. 11, 2011

Related U.S. Application Data

(60) Provisional application No. 61/104,434, filed on Oct. 10, 2008, provisional application No. 61/175,624, filed on May 5, 2009.

(51) Int. Cl.
*C07D 417/02* (2006.01)
*C07D 417/00* (2006.01)
*C07D 241/02* (2006.01)
*C07D 217/00* (2006.01)

(52) U.S. Cl.
USPC ........................... 544/367; 544/384; 546/146

(58) Field of Classification Search
USPC .................................. 544/367, 384; 546/146
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,630,200 A | 12/1971 | Higuchi | |
| 3,847,770 A | 11/1974 | Radlowe et al. | |
| 3,916,899 A | 11/1975 | Theeuwes et al. | |
| 4,008,719 A | 2/1977 | Theeuwes et al. | |
| 4,687,610 A | 8/1987 | Vassilatos | |
| 4,769,027 A | 9/1988 | Baker et al. | |
| 5,059,595 A | 10/1991 | Grazie | |
| 5,073,543 A | 12/1991 | Marshall et al. | |
| 5,120,548 A | 6/1992 | McClelland et al. | |
| 5,354,566 A | 10/1994 | Addesso et al. | |
| 5,591,767 A | 1/1997 | Morh et al. | |
| 5,627,165 A | 5/1997 | Glazier | |
| 5,639,476 A | 6/1997 | Oshlack et al. | |
| 5,674,533 A | 10/1997 | Santus et al. | |
| 5,733,566 A | 3/1998 | Lewis | |
| 7,291,620 B2 | 11/2007 | Coburn et al. | |
| 7,348,356 B2 | 3/2008 | Coburn et al. | |

| | | |
|---|---|---|
| 2005/0119227 A1 | 6/2005 | Cumming et al. |
| 2006/0178383 A1 | 8/2006 | Bischoff et al. |
| 2006/0229309 A1 | 10/2006 | Thompson et al. |
| 2007/0117793 A1 | 5/2007 | Ghosh et al. |
| 2007/0213316 A1 | 9/2007 | John et al. |
| 2007/0213331 A1 | 9/2007 | Dally et al. |
| 2008/0096942 A1 | 4/2008 | Tenbrink et al. |
| 2008/0153868 A1 | 6/2008 | Thompson et al. |

FOREIGN PATENT DOCUMENTS

| | | | |
|---|---|---|---|
| WO | WO2005016876 | * 12/2005 | ................. 514/235.5 |
| WO | WO 2006/103038 | 10/2006 | |
| WO | WO 2007/058583 | 5/2007 | |
| WO | WO 2007/058862 | 5/2007 | |
| WO | WO 2010/042892 | 4/2010 | |
| WO | WO 2010/059953 | 5/2010 | |
| WO | WO 2010/065861 | 6/2010 | |

OTHER PUBLICATIONS

PCT International Search Report for PCT/US2009/060132, completed Feb. 21, 2010.
A. K. Ghosh, et al., "Design of Potent Inhibitors for Human Brain Memapsin 2 (β-Secretase)," J. Am. Chem. Soc., 122:3522-3523 (2000).
L. Hong, et al., "Structure of the Protease Domain of Memapsin 2 (β-Secretase) Complexed with Inhibitor," Science, 290:150-153 (2000).
R. T. Turner III, et al., "Subsite Specificity of Memapsin 2 (β-Secretase): Implications for Inhibitor Design," Biochemistry, 40:10001-10006 (2001).
Arun K. Ghosh, et al., "Structure Based Design: Potent Inhibitors of Human Brain Memapsin 2 (β-Secretase)," J. Med. Chem., 44:2865-2868 (2001).
A. K. Ghosh, et al., "β-Secretase as a Therapeutic Target for Inhibitor Drugs," Curr. Med. Chem., 9:1135-1144 (2002).
Robert T. Turner, III, "Specificity of Memapsin 1 and Its Implications on the Design of Memapsin 2 (β-Secretase) Inhibitor Selectivity," Biochemistry, 41:8742-8746 (2002).
Lin Hong, et al., "Crystal Structure of Memapsin 2 (β-Secretase) in Complex with an Inhibitor OM00-3," Biochemistry, 41:10963-10967 (2002).
L. Hong, et al., "Memapsin 2 (β-Secretase) as a therapeutic target," Biochem. Soc. Trans., 30:530-534 (2002).
Jordan Tang, et al., "Study of Memapsin 2 (β-Secretase) and Strategy of Inhibitor Design," Journal of Molecular Neuroscience, 20:299-304 (2003).
G. Koelsch, et al., "Memapsin 2, a drug target for Alzheimer's disease," Biochemical Society Symposia, 70:213-220 (2003).
W.-P. Chang, et al., "In vivo inhibition of Aβ production by memapsin 2 (β-secretase) inhibitors," J. Neurochem., 89:1409-1416 (2004).
Robert T. Turner, III, et al., "Structural Locations and Functional Roles of New Subsites $S_5$, $S_6$ and $S_7$ in Memapsin 2 (β-Secretase )," Biochemistry, 44:105-112 (2005).
Gerald Koelsch, et al., "Analysis of Amyloid Precursor Protein Processing Protease β-Secretase: Tools for Memapsin 2 (β-Secretase) Inhibition Studies," Amyloid Precursor Protein 41-50 (2005).
Arun K. Ghosh, et al., "Structure-based design of cycloamide-urethane-derived novel inhibitors of human brain memapsin 2 (β-secretase)," Bioorg. Med. Chem. Lett., 15:15-20 (2005).

(Continued)

*Primary Examiner* — Samantha Shterengarts
(74) *Attorney, Agent, or Firm* — Purdue Research Foundation

(57) ABSTRACT

Described herein are compounds, and pharmaceutical compositions, methods, and uses thereof for treating Alzheimer's disease.

23 Claims, No Drawings

(56) References Cited

OTHER PUBLICATIONS

Arun K. Ghosh, et al., "Recent Development of Structure-Based β-Secretase Inhibitors for Alzheimer's Disease," Curr. Top. Med. Chem., 5:1609-1622 (2005).

Arun K. Ghosh, et al., "Design, Synthesis and X-ray Structure of Protein-Ligand Complexes: Important Insight into Selectivity of Memapsin 2 (β-Secretase) Inhibitors," J. Am. Chem. Soc., 128:5310-5311 (2006).

Arun K. Ghosh, et al., "Design, Synthesis and X-ray Structure of Potent Memapsin 2 (β-Secretase) Inhibitors with Isophthalamide Derivatives as the $P_2$-$P_3$-Ligands," J. Med. Chem., 50:2399-2407 (2007).

Arun K. Ghosh, et al., "Memapsin 2 (β-Secretase) Inhibitor Drug, between Fantasy and Reality," Curr. Alz. Res., 4:418-422 (2007).

Arun K. Ghosh, et al., "Potent memapsin 2 (beta-secretase) inhibitors: Design, synthesis, protein-ligand X-ray structure, and in vivo evaluation," Bioorg. Med. Chem. Lett., 18:1031-1036 (2008).

Arun K. Ghosh, et al., "Memapsin 2 (Beta-Secretase) Inhibitors: Drug Development," Curr. Alz. Res., 5:121-131 (2008).

Arun K. Ghosh, et al., "β-Secretase as a Therapeutic Target for Alzheimer's Disease," Neurotherapeutics, 5:399-408 (2008).

Polgar et al., "Virtual Screening for β-Secretase (BACE1) Inhibitors Reveals the Importance of Protonation States at Asp32 and Asp228," J. Med. Chem., 48:3749-3755 (2005).

European Search Report for EP Patent Application No. 09819930; communicated Aug. 16, 2012, 3 pages.

Stachel S J et al: "Structure-based design of potent and selective cell-permeable inhibitors of human beta-secretase (BACE-1)," Journal of Medicinal Chemistry, American Chemical Society, US, vol. 47, No. 26, Nov. 11, 2004, pp. 6447-6450.

Katharine Holloway et al: "Evaluating scoring functions for docking and designing beta-secretase inhibitors", Bioorganic & Medicinal Chemistry Letters, Pergamon, Elsevier Science, GB, vol. 17, No. 3, Jan. 19, 2007, pp. 823-827.

Kortum et al: "Potent and selective isophthalamide S2 hydroxyethylamine inhibitors of BACE1," Bioorganic & Medicinal Chemistry Letters, Pergamon, Elsevier Science, GB, vol. 17, No. 12, Jun. 15, 2007, pp. 3378-3383.

"Statine-derived tetrapeptide inhibitors of beta-secretase," Expert Opinion on Therapeutic Patents, Jun. 1, 2001, pp. 1047-1050.

\* cited by examiner

COMPOUNDS FOR TREATMENT OF ALZHEIMER'S DISEASE

CROSS REFERENCE TO RELATED APPLICATIONS

This application is a U.S. national application under 35 U.S.C. §371 (b) of International Application Serial No. PCT/US2009/060132 filed Oct. 9, 2009, which claims priority to U.S. Provisional Application Ser. No. 61/104,434 filed on Oct. 10, 2008 and U.S. Provisional Application Ser. No. 61/175,624 filed May 5, 2009, the entire disclosures of which are hereby incorporated by reference.

GOVERNMENT RIGHTS

This invention was made with government support under AG018933 awarded by The National Institutes of Health. The government has certain rights in the invention.

TECHNICAL FIELD

The invention described herein pertains to compounds and compositions for the treatment of Alzheimer's disease.

BACKGROUND AND SUMMARY OF THE INVENTION

Alzheimer's disease is a progressive mental deterioration in a human resulting in loss of memory, confusion and disorientation, as well as, behavioral problems such as anxiety. Alzheimer's disease accounts for the majority of senile dementias and is a leading cause of death in adults (Anderson, R. N., *Natl. Vital Stat. Rep.* 49.1-87 (2001)). The disclosure of the foregoing is incorporated herein in its entirety by reference. In addition, the entirety of the disclosures of each of the publications cited herein are incorporated herein by reference. Currently-used treatments offer a small symptomatic benefit; no treatments to delay or halt the progression of the disease are as yet available.

The cause and progression of Alzheimer's disease are not well understood. Research indicates that the disease is associated with plaques and tangles in the brain (Tiraboschi P., et al., 2004, *Neurology* 62 (11): 1984-9). Histologically, the brain of persons afflicted with Alzheimer's disease is characterized by a distortion of the intracellular neurofibrils and the presence of senile plaques composed of granular or filamentous argentophilic masses with an amyloid protein core, largely due to the accumulation of β-amyloid protein (Aβ) in the brain. Aβ accumulation plays a role in the pathogenesis and progression of the disease (Selkoe, D. J., *Nature* 399: 23-31 (1999)) and is a proteolytic fragment of amyloid precursor protein (APP). APP is cleaved initially by β-secretase (also referred to as memapsin 2) followed by γ-secretase to generate Aβ (Lin, X., et al., *Proc. Natl. Acad. Sci. USA* 97:1456-1460 (2000); De Stropper, B., et al., *Nature* 391: 387-390 (1998)). Without being bound by theory, it is believed that one approach to the treatment of Alzheimer's disease is to inhibit the production of Aβ.

It has been discovered herein that the compounds described herein are useful for treating Alzheimer's disease. In one embodiment of the invention, compounds are described herein for treating Alzheimer's disease. In another embodiment of the invention, pharmaceutical compositions are described herein for treating Alzheimer's disease where the pharmaceutical compositions include one or more of the compounds described herein in a therapeutically effective amount. In another embodiment of the invention, methods for treating Alzheimer's disease in a patient in need of relief are described herein, where the methods include the step of administering a therapeutically effective amount of one or more compounds and/or one or more pharmaceutical compositions described herein. In another embodiment of the invention, uses of the one or more compounds and/or one or more pharmaceutical compositions described herein in the manufacture of a medicament for treating Alzheimer's disease are described herein. Without being bound by theory, it is believed that the efficacy of the compounds herein described may be due at least in part to their potency in inhibiting the proteolytic activity of the enzyme memapsin 2.

It is to be understood that the compounds described herein may be used alone or in combination with other compounds useful for treating Alzheimer's disease, including those compounds that may operate by the same or different modes of action. It is also to be understood that the compounds described herein may be used in combination with other compounds to improve cognitive properties as well as anxiolytics and antipsychotics to control behavior.

DETAILED DESCRIPTION

In one embodiment of the invention, a compound of the formula (I) is described

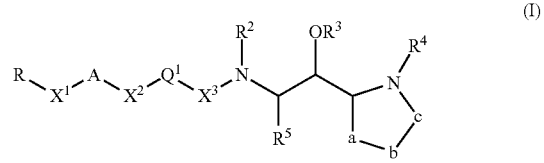

or a pharmaceutically acceptable salt thereof; wherein a, b, and c, are each independently selected from optionally substituted alkylene, $NR^6$, W, C(W), S(O), $S(O)_2$, or a combination thereof, where W is O or S; or a and b, b and c, or a and c are taken together with the attached atoms to form an optionally substituted bicyclic ring; providing that a-b-c does not comprise W—W, or C(W)—W—C(W);

$Q^1$ is a divalent carbocycle, heterocycle, unsaturated heterocycle, aryl, or heteroaryl, each of which is optionally substituted;

$X^2$ is $NR^1$, C(O), S(O), $S(O)_2$, $NR^1$—C(O), $NR^1$—S(O), $NR^1$—$S(O)_2$, optionally substituted alkylene, or optionally substituted alkylenoxy;

$X^3$ is C(O), S(O), $S(O)_2$ or $CHR^1$;

R is alkyl, heteroalkyl, cycloalkyl, heterocycloalkyl, aryl, arylalkyl, heteroaryl, or heteroarylalkyl, each of which is optionally substituted;

$X^1$ is optionally substituted alkylene, such as methylene or substituted methylene;

A is O or $NR^1$; or A is a nitrogen atom, and A and $X^1$ are taken together to form an optionally substituted heterocycle $R^1$ is independently selected in each instance from hydrogen, alkyl, heteroalkyl, cycloalkyl, heterocycloalkyl, aryl, arylalkyl, heteroaryl, or heteroarylalkyl, each of which is optionally substituted;

$R^2$, $R^3$, and $R^4$ are in each instance independently selected from the group consisting of hydrogen and a prodrug forming group;

$R^5$ is alkyl, alkenyl, heteroalkyl, cycloalkyl, heterocycloalkyl, aryl, arylalkyl, heteroaryl, or heteroarylalkyl, each of which is optionally substituted;

$R^6$ is hydrogen, $OR^7$, $S(O)R^7$, $S(O)_2R^7$, $C(O)R^8$, $C(O)OR^7$, $C(O)NR^9R^{10}$, $S(O)NR^9R^{10}$, $S(O)_2NR^9R^{10}$, alkyl, alkenyl, heteroalkyl, cycloalkyl, heterocycloalkyl, aryl, arylalkyl, heteroaryl, or heteroarylalkyl, each of which is optionally substituted;

$R^7$ is in each instance independently selected from the group consisting of alkyl, alkenyl, heteroalkyl, cycloalkyl, heterocycloalkyl, aryl, arylalkyl, heteroaryl, and heteroarylalkyl, each of which is optionally substituted;

$R^8$ is in each instance independently selected from hydrogen, or selected from the group consisting of, alkyl, alkenyl, heteroalkyl, cycloalkyl, heterocycloalkyl, aryl, arylalkyl, heteroaryl, and heteroarylalkyl, each of which is optionally substituted; and $R^9$ and $R^{10}$ are in each instance independently selected from hydrogen, or selected from the group consisting of alkyl, alkenyl, heteroalkyl, cycloalkyl, heterocycloalkyl, aryl, arylalkyl, heteroaryl, alkylsulfonyl, arylsulfonyl, and heteroarylalkyl, each of which is optionally substituted; or $R^9$ and $R^{10}$ and the attached nitrogen form an optionally substituted heterocycle.

In another embodiment of formula (I), a is C(O), or alkylene or C(O)alkylene, each of which is optionally substituted. In another embodiment of formula (I), b is optionally substituted alkylene, O, S(O), S(O)$_2$, or $NR^6$. In another embodiment of formula (I), c is alkylene or C(O)alkylene each of which is optionally substituted, or c is C(O), S(O), S(O)$_2$, or $NR^6$.

In another embodiment of formula (I), a is C(O), b is $NR^6$, c is optionally substituted alkylene, and $R^6$ is arylalkyl or alkyl.

In another embodiment of formula (I), a, b, and c are taken together with the attached atoms to form pyrrolidine, oxazolidine, isoxazolidine, pyrazolidine, morpholine, piperidine, piperazine, such as piperazinone and the like, tetrahydroquinoline, tetrahydroisoquinoline, tetrahydroquinazoline, benzopyrazine, homopiperidine, or homopiperazine, each of which is optionally substituted. In another embodiment, said substituents include one or more substituents selected from substituted benzyl, optionally substituted phenyl, fluoro, fluoroalkyl, and the like. In another embodiment of formula (I), a is C(O), b is optionally substituted alkylene, c is $NR^6$, and $R^6$ is arylalkyl are described.

In another embodiment of formula (I), a and b and the attached atoms form an optionally substituted fused bicyclic ring. In another embodiment of formula (I), b and c and the attached atoms form an optionally substituted fused bicyclic ring. In another embodiment of formula (I), a and c and the attached atoms form an optionally substituted bicyclic ring.

In another embodiment, compounds of formula (II)

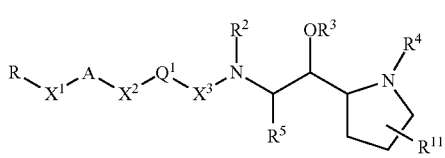

(II)

or a pharmaceutically acceptable salt thereof are described, wherein $R^{11}$ is hydrogen, or $R^{11}$ is alkyl, alkenyl, heteroalkyl, alkoxyl, thioalkyl, haloalkyl, cycloalkyl, heterocycloalkyl, aryl, arylalkyl, heteroaryl, or heteroarylalkyl, each of which is optionally substituted. In another embodiment, $R^{11}$ is optionally substituted benzyl. In another embodiment, $R^{11}$ is optionally substituted benzyl attached at C-3. In another embodiment, $R^{11}$ is optionally substituted benzyl attached at C-4.

In another embodiment, compounds of formula (IIa)

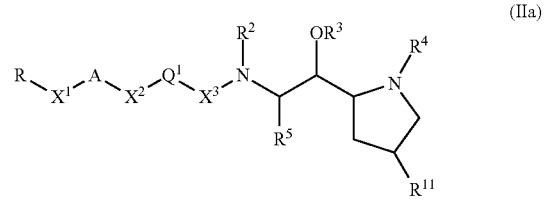

(IIa)

or a pharmaceutically acceptable salt thereof are described; wherein $R^{11}$ is hydrogen, or $R^{11}$ is alkyl, alkenyl, heteroalkyl, alkoxyl, thioalkyl, haloalkyl, cycloalkyl, heterocycloalkyl, aryl, arylalkyl, heteroaryl, or heteroarylalkyl, each of which is optionally substituted. In another embodiment, $R^{11}$ is optionally substituted benzyl.

In another embodiment, compounds of formula (IIb)

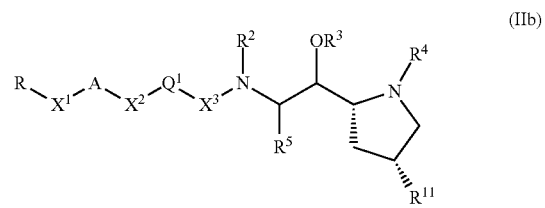

(IIb)

or a pharmaceutically acceptable salt thereof are described; wherein $R^{11}$ is hydrogen, or $R^{11}$ is alkyl, alkenyl, heteroalkyl, alkoxyl, thioalkyl, haloalkyl, cycloalkyl, heterocycloalkyl, aryl, arylalkyl, heteroaryl, or heteroarylalkyl, each of which is optionally substituted. In another embodiment, $R^{11}$ is optionally substituted benzyl.

In another embodiment, compounds of formula (IIc)

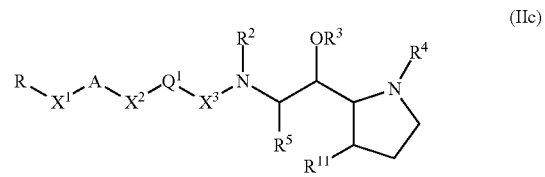

(IIc)

or a pharmaceutically acceptable salt thereof are described; wherein $R^{11}$ is hydrogen, or $R^{11}$ is alkyl, alkenyl, heteroalkyl, alkoxyl, thioalkyl, haloalkyl, cycloalkyl, heterocycloalkyl, aryl, arylalkyl, heteroaryl, or heteroarylalkyl, each of which is optionally substituted. In another embodiment, $R^{11}$ is optionally substituted benzyl.

In each of formulae (II), each of R, $X^1$, A, $X^2$, $Q^1$, $X^3$, $R^1$, $R^2$, $R^3$, $R^4$, and $R^5$ are as described in each of the embodiments described herein. It is to be understood that additional embodiments of the invention are described herein where for example, R may be independently selected from an embodiment described herein, and $X^1$ may be independently selected from the same or different embodiment. Those embodiments and each other embodiment that may be indentified by such a selection of any of R, $X^1$, A, $X^2$, $Q^1$, $X^3$, $R^1$, $R^2$, $R^3$, $R^4$, and $R^5$ are understood to be described herein. It is further to be understood that each of R, $X^1$, A, $X^2$, $Q^1$, $X^3$, $R^1$, $R^2$, $R^3$, $R^4$, $R^5$, $R^6$, $R^7$, $R^8$, $R^9$, $R^{10}$, $R^{11}$, W, Y, $Y^1$, $Y^2$, Z, a, b, and c recited in any of formulae (III), and other formulae and/or embodiments described herein may be independently selected from the same or different embodiment described herein.

In another embodiment, compounds of formula (III)

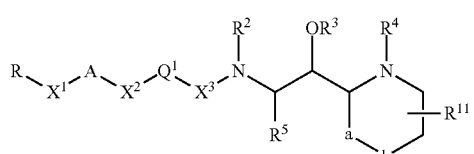

(III)

or a pharmaceutically acceptable salt thereof are described.

In another embodiment, compounds of formula (IIIa)

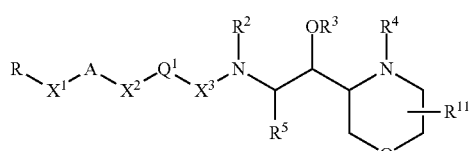

(IIIa)

or a pharmaceutically acceptable salt thereof are described.

In another embodiment, compounds of formula (IIIb)

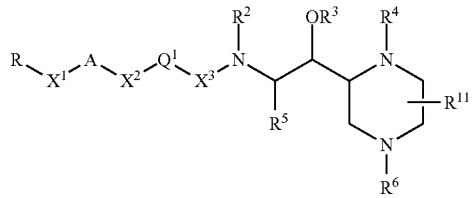

(IIIb)

or a pharmaceutically acceptable salt are described. In another embodiment, $R^6$ is H.

In another embodiment, compounds of formula (IIIc)

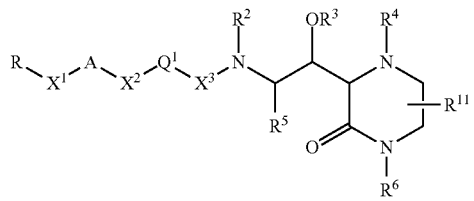

(IIIc)

or a pharmaceutically acceptable salt thereof are described. In another embodiment, $R^6$ is H.

In another embodiment, compounds of formula (IIId)

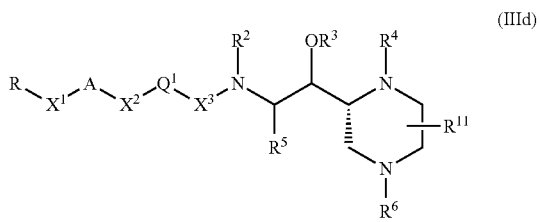

(IIId)

or a pharmaceutically acceptable salt thereof are described. In another embodiment, $R^6$ is H.

In another embodiment, compounds of formula (IIIe)

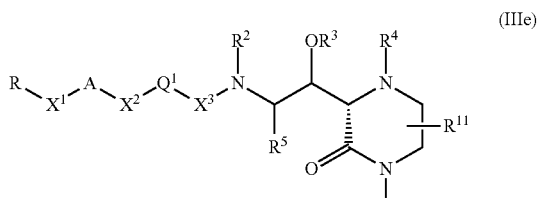

(IIIe)

or a pharmaceutically acceptable salt thereof are described. In another embodiment, $R^6$ is H.

In another embodiment, compounds of formula (IIIf)

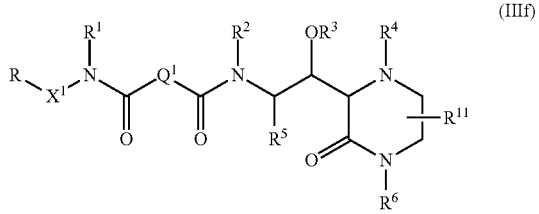

(IIIf)

or a pharmaceutically acceptable salt thereof are described.

In each of formulae (III), each of R, $X^1$, A, $X^2$, $Q^1$, $X^3$, $R^1$, $R^2$, $R^3$, $R^4$, $R^5$, $R^6$, $R^{11}$, a and b are as described in each of the embodiments described herein.

In another embodiment of formula (III), a is optionally substituted alkylene, or C(O), and b is O, S(O), S(O)$_2$, or $NR^6$. In another embodiment, $R^6$ is optionally substituted benzyl. In another embodiment, $R^6$ is optionally substituted benzyl, and $R^{11}$ is H. In another embodiment, $R^6$ is optionally substituted benzyl, and $R^{11}$ is alkyl. In another embodiment, $R^6$ is optionally substituted alkyl, and $R^{11}$ is H. In another embodiment, $R^6$ is optionally substituted alkyl, and $R^{11}$ is alkyl. In another embodiment, $R^6$ is optionally substituted branched alkyl, and $R^{11}$ is H.

In another embodiment of each of the foregoing formulae (II) and/or (III), $R^{11}$ is selected from halo, such as fluoro, and the like, aryloxy, such as phenyloxy, and the like; arylalkyloxy, such as benzyloxy, and the like; arylamino, such as phenylamino, and the like; arylalkylamino, such as benzylamino, and the like; alkoxy, such as methoxy, and the like; alkyl, such as methyl, and the like; alkoxy, such as methoxy, and the like; alkylamino, such as methylamino, dimethyamino, and the like; alkylsulfonyl, such as methylsulfonyl, and the like; aminosulfonyl, such as $H_2N-SO_2$, and the like; and heteroalkyl, such as methoxymethyl, and the like; each of which is optionally substituted, such as fluoroalkyl, hydroxyalkyl, and the like.

In another embodiment, compounds of formula (IV)

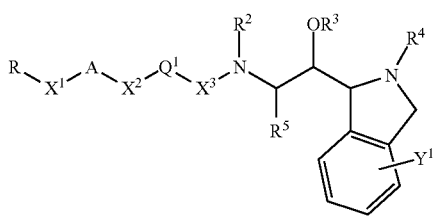

or a pharmaceutically acceptable salt thereof are described, wherein $Y^1$ represents from 1 to 3 optional substituents independently selected in each instance from the group consisting of hydroxy, halo, alkoxy, C(O)-alkyl, C(O)-aryl, C(O)-alkoxy, C(O)-amino, S(O)-alkyl, S(O)$_2$-alkyl, S(O)-aryl, S(O)$_2$-aryl, alkyl, heteroalkyl, cycloalkyl, alkenyl, amino, alkylene-amino, aryl, arylalkyl, heteroaryl, and heteroarylalkyl, each of which is optionally substituted.

In one embodiment, compounds of formula (V)

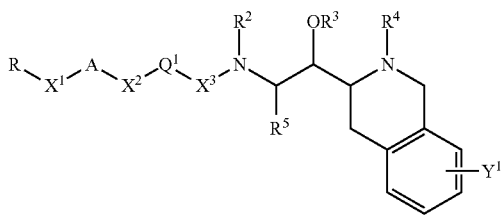

or a pharmaceutically acceptable salt thereof are described, wherein $Y^1$ represents from 1 to 3 optional substituents independently selected in each instance from the group consisting of hydroxy, halo, alkoxy, C(O)-alkyl, C(O)-aryl, C(O)-alkoxy, C(O)-amino, S(O)-alkyl, S(O)$_2$-alkyl, S(O)-aryl, S(O)$_2$-aryl, alkyl, heteroalkyl, cycloalkyl, alkenyl, amino, alkylene-amino, aryl, arylalkyl, heteroaryl, and heteroarylalkyl, each of which is optionally substituted.

In another embodiment, compounds of any of formulae (I) to (V) are described, wherein $Q^1$ is 1,3-phenylene, 2,6-pyridinylene, 2,4-pyridylene, or 3,5-pyridylene, each of which is optionally substituted.

In another embodiment, compounds of any of formulae (I) to (V) are described, wherein $Q^1$ is 1,3-phenylene, optionally substituted with from 1 to 3 substituents selected from hydroxy, halo, alkoxy, C(O)-alkyl, C(O)-aryl, C(O)-alkoxy, C(O)-amino, S(O)-alkyl, S(O)$_2$-alkyl, S(O)-aryl, S(O)$_2$-aryl, alkyl, heteroalkyl, cycloalkyl, alkenyl, amino, alkylene-amino, aryl, arylalkyl, heteroaryl, and heteroarylalkyl, each of which is optionally substituted.

In another embodiment, compounds of any of formulae (I) to (V) are described, wherein $X^2$-$Q^1$-$X^3$ is selected from the following divalent formulae

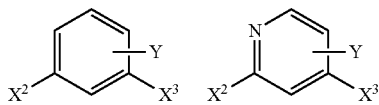 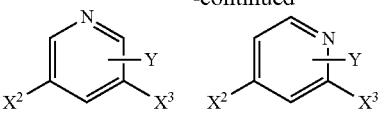

where Y represents from 1 to 3 optional substituents independently selected in each instance from the group consisting of hydroxy, halo, or alkoxy, C(O)-alkyl, C(O)-aryl, C(O)-alkoxy, C(O)-amino, S(O)-alkyl, S(O)$_2$-alkyl, S(O)-aryl, S(O)$_2$-aryl, alkyl, heteroalkyl, cycloalkyl, alkenyl, amino, alkylene-amino, aryl, arylalkyl, heteroaryl, and heteroarylalkyl, each of which is optionally substituted. In another embodiment, Y represents from 1 to 3 optional substituents independently selected in each instance from the group consisting of halo, OR$^8$, C(O)R$^8$, C(O)NR$^9$R$^{10}$, C(O)OR$^8$, S(O)R$^8$, S(O)$_2$R$^8$, alkyl, heteroalkyl, haloalkyl, cycloalkyl, alkenyl, NR$^9$R$^{10}$, alkylene-NR$^9$R$^{10}$, alkylene-OR$^8$, aryl, arylalkyl, heteroaryl and heteroarylalkyl.

In another embodiment, compounds of any of formulae (I) to (V) are described, wherein $X^2$-$Q^1$-$X^3$ is

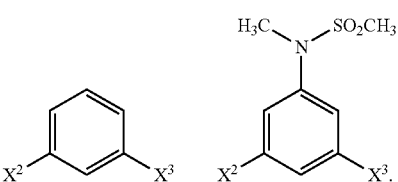

wherein $X^1$ and $X^2$ are as defined in each of the foregoing embodiments.

In another embodiment, compounds of any of formulae (I) to (V) are described, wherein $X^2$-$Q^1$-$X^3$ is

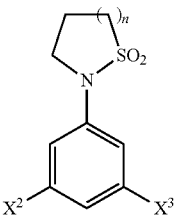

wherein $X^1$ and $X^2$ are as defined in each of the foregoing embodiments; and n is 1 or 2.

In another embodiment, compounds of any of formulae (I) to (V) are described, wherein $Q^1$ is optionally substituted divalent phenyl. In one variation, said substituents are selected from pyrrolyl, furanyl, thienyl, imidazlyl, pyrazolyl, oxazolyl, thiazolyl, isoxazolyl, isothiazolyl, pyridinyl, pyridazinyl, pyrimidinyl, and pyrazinyl, each of which is optionally substituted.

In another embodiment, compounds of any of formulae (I) to (V) are described, wherein $Q^1$ is optionally substituted divalent phenyl. In one variation, said substituents are selected from tetrahydrofuranyl, bistetrahydrofuranyl, tetrahydropyranyl, morpholinyl, piperdinyl, and piperazinyl, each of which is optionally substituted.

In another embodiment, compounds of any of formulae (I) to (V) are described, wherein $X^2$-$Q^1$-$X^3$ is selected from the following divalent radicals

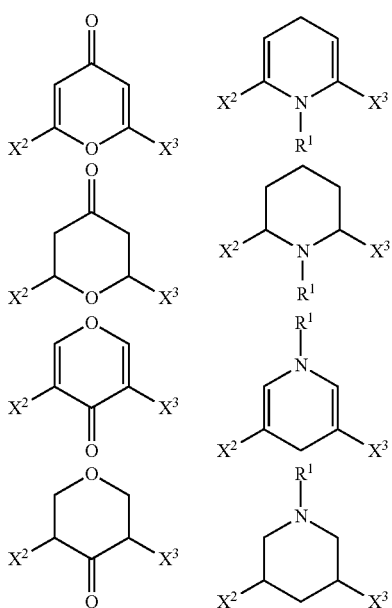

are described, where R[1] is as defined herein; and X[2] and X[3] are each C(O). In another embodiment R[1] is hydrogen or alkyl.

In another embodiment, compounds of any of formulae (I) to (V), or any of the foregoing embodiments are described, wherein X[2] is C(O). In another embodiment, X[2] is CHOH, CHOCH$_3$. In another embodiment, X[2] is C(O), S(O), S(O)$_2$, or optionally substituted alkylene;

In another embodiment, compounds of any of formulae (I) to (V), or any of the foregoing embodiments are described, wherein R[5] is optionally substituted arylalkyl are described. In another embodiment, R[5] is optionally substituted benzyl. In another embodiment, R[5] is haloalkyl. In another embodiment, R[5] is fluoroalkyl. In another embodiment, R[5] is branched alkyl. In another embodiment, R[5] is isobutyl or neopentyl. In another embodiment, R[5] is branched fluoroalkyl. In another embodiment, R[5] is 2-trifluoromethylpropyl. In another embodiment, R[5] is benzyl, furanylmethyl, thienylmethyl, or pyrazolylmethyl, each of which is optionally substituted. In another embodiment, R[5] is benzyl or substituted benzyl, where at least one of said substituents is selected from halo, such as fluoro; alkyl, such as methyl, or a combination thereof. In another embodiment, R[5] is aryl, arylalkyl, heteroaryl, or heteroarylalkyl, each of which is substituted, where at least one of said substituents is selected from fluoro and alkyl.

In another embodiment, compounds of any of formulae (I) to (V), or any of the foregoing embodiments are described, wherein the alkyl is methyl.

In another embodiment, compounds of any of formulae (I) to (V), or any of the foregoing embodiments are described, wherein R is heteroaryl, aryl, heteroarylalkyl or arylalkyl, each of which is optionally substituted.

In another embodiment, compounds of any of formulae (I) to (V), or any of the foregoing embodiments are described, wherein X[1] is CH$_2$, A is NR[1], R[1] is alkyl, and R is optionally substituted heteroaryl are described. In another embodiment, R is heteroaryl, A is a nitrogen atom, and A and X[1] are taken together to form an optionally substituted heterocycle. In another embodiment, R is arylalkyl, A is a nitrogen atom, and A and X[1] are taken together to form an optionally substituted heterocycle. In another embodiment, A is NH or N-alkyl, and X[1]—R are taken together to form arylalkyl or heteroarylalkyl, each of which is optionally substituted.

In another embodiment, compounds of any of formulae (I) to (V), or any of the foregoing embodiments are described wherein A is NH or N-alkyl, and X[1]—R are taken together to form a radical of the formula:

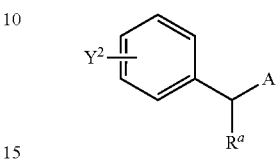

where Y[2] and R[a] are each independently selected from alkyl or heteroalkyl, each of which is optionally substituted. In another embodiment, Y[2] and R[a] are each independently selected from alkyl, such as methyl, ethyl, and the like; haloalkyl, such as fluoromethyl, chloromethyl, and the like; alkoxyalkyl, such as methoxymethyl, and the like; and aminoalkyl, such as H$_2$N—CH$_2$, methylaminomethyl, dimethylaminomethyl, and the like. In another embodiment, R[a] is methyl. In another embodiment, Y[2] is H.

In another embodiment, compounds of any of formulae (I) to (V), or any of the foregoing embodiments are described wherein A is NH or N-alkyl, and X[1]—R are taken together to form a radical of the formula

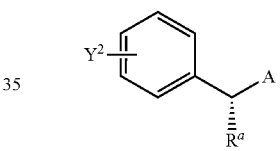

where Y[2] and R[a] are each independently selected from H, and alkyl and heteroalkyl, each of which is optionally substituted. In another embodiment, Y[2] and R[a] are each independently selected from alkyl, such as methyl, ethyl, and the like; haloalkyl, such as fluoromethyl, chloromethyl, and the like; alkoxyalkyl, such as methoxymethyl, and the like; and aminoalkyl, such as H$_2$N—CH$_2$, methylaminomethyl, dimethylaminomethyl, and the like. In another embodiment, R[a] is methyl. In another embodiment, Y[2] is H.

In another embodiment, compounds of any of formulae (I) to (V), or any of the foregoing embodiments are described wherein A is NH or N-alkyl, and X[1]—R are taken together to form a radical of the formula

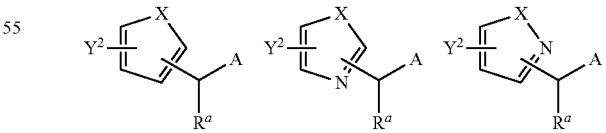

where X is NR[1], O, or S; and Y[2] and R[a] are each independently selected from H, and alkyl and heteroalkyl, each of which is optionally substituted. In another embodiment, Y[2] and R[a] are each independently selected from alkyl, such as methyl, ethyl, and the like; haloalkyl, such as fluoromethyl, chloromethyl, and the like; alkoxyalkyl, such as methoxymethyl, and the like;

and aminoalkyl, such as $H_2N-CH_2$, methylaminomethyl, dimethylaminomethyl, and the like.

In another embodiment, compounds of any of formulae (I) to (V), or any of the foregoing embodiments are described wherein A is NH or N-alkyl, and $X^1$—R are taken together to form a radical of the formula:

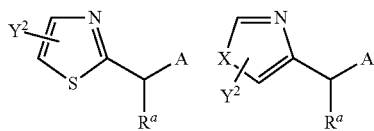

where X is O or S; and $Y^2$ and $R^a$ are each independently selected from H, and alkyl and heteroalkyl, each of which is optionally substituted. In another embodiment, $Y^2$ and $R^a$ are each independently selected from alkyl, such as methyl, ethyl, and the like; haloalkyl, such as fluoromethyl, chloromethyl, and the like; alkoxyalkyl, such as methoxymethyl, and the like; and aminoalkyl, such as $H_2N-CH_2$, methylaminomethyl, dimethylaminomethyl, and the like.

In another embodiment, compounds of any of formulae (I) to (V), or any of the foregoing embodiments are described wherein R—$X^1$-A-$X^2$ are taken together to form a radical of the formula:

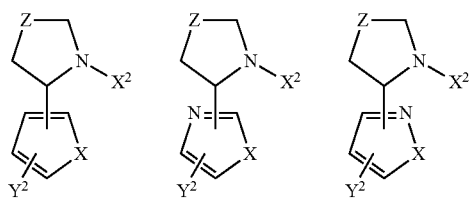

where Z is $CH_2$, $NR^1$, O, or S; X is $NR^1$, O, or S; and $Y^2$ and $R^a$ are each independently selected from H, and alkyl and heteroalkyl, each of which is optionally substituted. In another embodiment, $Y^2$ and $R^a$ are each independently selected from alkyl, such as methyl, ethyl, and the like; haloalkyl, such as fluoromethyl, chloromethyl, and the like; alkoxyalkyl, such as methoxymethyl, and the like; and aminoalkyl, such as $H_2N-CH_2$, methylaminomethyl, dimethylaminomethyl, and the like.

In another embodiment, compounds of any of formulae (I) to (V), or any of the foregoing embodiments are described wherein R—$X^1$-A-$X^2$ are taken together to form a radical of the formula:

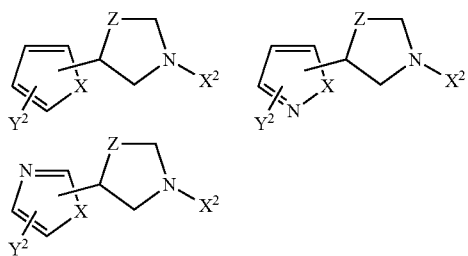

where Z is $CH_2$, NR, O, or S; X is $NR^1$, O, or S; and $Y^2$ and $R^a$ are each independently selected from H, and alkyl and heteroalkyl, each of which is optionally substituted. In another embodiment $Y^2$ and $R^a$ are each independently selected from alkyl, such as methyl, ethyl, and the like; haloalkyl, such as fluoromethyl, chloromethyl, and the like; alkoxyalkyl, such as methoxymethyl, and the like; and aminoalkyl, such as $H_2N-CH_2$, methylaminomethyl, dimethylaminomethyl, and the like.

In another embodiment, compounds of any of formulae (I) to (V), or any of the foregoing embodiments are described wherein R—$X^1$-A-$X^2$ are taken together to form a radical of the formula:

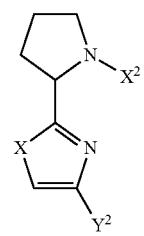

where X is O or S; and $Y^2$ and $R^a$ are each independently selected from H, and alkyl and heteroalkyl, each of which is optionally substituted. In another embodiment, $Y^2$ and $R^a$ are each independently selected from alkyl, such as methyl, ethyl, and the like; haloalkyl, such as fluoromethyl, chloromethyl, and the like; alkoxyalkyl, such as methoxymethyl, and the like; and aminoalkyl, such as $H_2N-CH_2$, methylaminomethyl, dimethylaminomethyl, and the like.

In another embodiment, compounds of any of formulae (I) to (V), or any of the foregoing embodiments are described wherein R—$X^1$-A-$X^2$ are taken together to form a radical of the formula:

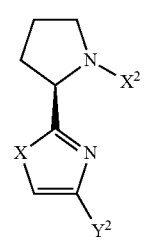

where X is O or S; and $Y^2$ and $R^a$ are each independently selected from H, and alkyl and heteroalkyl, each of which is optionally substituted. In another embodiment, $Y^2$ and $R^a$ are each independently selected from alkyl, such as methyl, ethyl, and the like; haloalkyl, such as fluoromethyl, chloromethyl, and the like; alkoxyalkyl, such as methoxymethyl, and the like; and aminoalkyl, such as $H_2N-CH_2$, methylaminomethyl, dimethylaminomethyl, and the like.

In another embodiment, compounds of formula

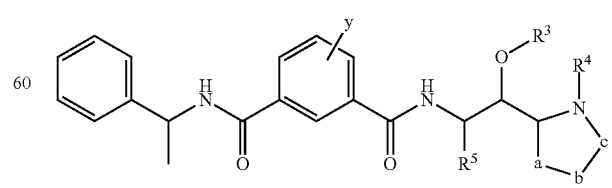

are described, wherein a, b, c, $R^3$, $R^4$, and $R^5$ are as described in any of the foregoing embodiments.

In another embodiment, compounds of formula

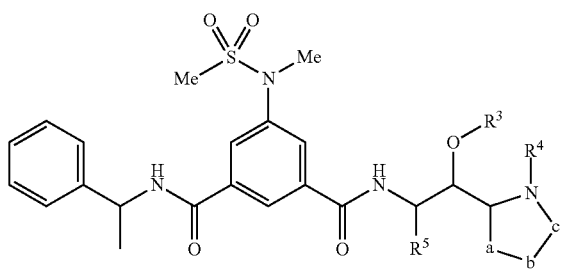

are described, wherein a, b, c, $R^3$, $R^4$, and $R^5$ are as described in any of the foregoing embodiments.

In another embodiment, compounds of formula

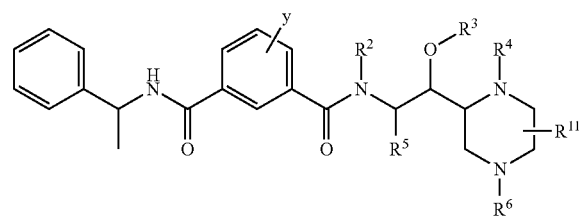

are described, wherein Y, $R^2$, $R^3$, $R^4$, $R^5$, $R^6$, and $R^{11}$ are as described in any of the foregoing embodiments.

In another embodiment, compounds of formula

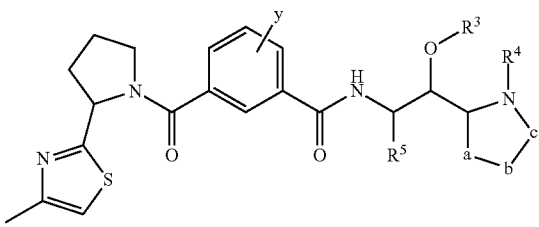

are described, wherein a, b, c, y, $R^3$, $R^4$, and $R^5$ are as described in any of the foregoing embodiments.

In another embodiment, compounds of any of formulae (I) to (V), or any of the foregoing embodiments are described wherein $R^{11}$ is optionally substituted arylalkyl, including benzyl, phenylethyl, and substituted variants thereof, such as benzyl and phenylethyl substituted with electron donating groups, including but not limited to alkoxy, such as methoxy.

In another embodiment, compounds of any of formulae (I) to (V), or any of the foregoing embodiments are described wherein a is C(O) and b is $NR^6$. In another embodiment, a is C(O), b is $NR^6$, and c is optionally substituted $C_2$-$C_3$ alkylene. In another embodiment, $R^6$ is optionally substituted arylalkyl, including but not limited to benzyl and substituted variants thereof. In another embodiment, $R^6$ is optionally substituted alkyl, including but not limited to iso-butyl and substituted variants thereof.

In another embodiment, any compound described in any one of the preceding embodiments has the following stereochemical configuration:

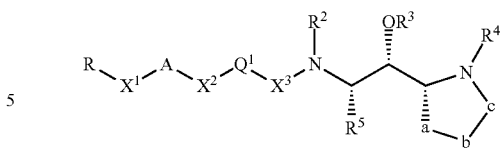

In another embodiment, compounds of any of formulae (I) to (V), or any of the foregoing embodiments are described wherein $X^2$ and $X^3$ are C(O) are described.

In another embodiment, compounds of any of formulae (I) to (V), or any of the foregoing embodiments are described where $R^5$ is branched alkyl, halosubstituted branched alkyl, benzyl, or halosubstituted benzyl.

In another embodiment, compounds of any of formulae (I) to (V), or any of the foregoing embodiments are described where each of $R^2$, $R^3$, and $R^4$ is hydrogen.

In another embodiment, compounds of any of formulae (I) to (V), or any of the foregoing embodiments are described where $Q^1$ is divalent benzene, or 4-substituted divalent benzene.

It is also appreciated that in the foregoing embodiments, certain aspects of the compounds are presented in the alternative, such as selections for any one or more of R, $X^1$, A, $X^2$, $Q^1$, $X^3$, $R^1$, $R^2$, $R^3$, $R^4$, $R^5$, $R^6$, $R^7$, $R^8$, $R^9$, $R^{10}$, $R^{11}$, W, Y, $Y^1$, $Y^2$, Z, a, b, and c. It is therefore to be understood that various alternate embodiments of the invention include individual members of those lists, as well as the various subsets of those lists. Each of those combinations is to be understood to be described herein by way of the lists.

It is appreciated that compounds described herein can exist in unsolvated forms as well as solvated forms, including hydrated forms. It is therefore to be understood that the solvated forms and unsolvated forms are encompassed within the scope of the each of the various illustrative embodiments of the invention described herein. It is further appreciated that compounds described herein can exist in an amorphous form or any of various multiple crystalline or other morphological forms. It is therefore to be understood that all physical forms are encompassed within the scope of the each of the various illustrative embodiments of the invention described herein.

It is also to be understood that any corresponding pharmaceutically acceptable salt is also included in each of the illustrative embodiments described herein. In addition, it is also to be understood that prodrug derivatives of the compounds described herein are included in each of the illustrative embodiments described herein.

It is also to be understood that the foregoing compounds represent all isotopes at each locus. For example, in each case, each hydrogen is independently selected from $^1H$, $^2H$, or $^3H$; each carbon is independently selected from $^{11}C$, $^{12}C$, $^{13}C$, or $^{14}C$; and the like.

As used herein, the term "aryl" includes monocyclic and polycyclic aromatic carbocyclic and aromatic heterocyclic groups, each of which may be optionally substituted. As used herein, the term "heteroaryl" includes aromatic heterocyclic groups, each of which may be optionally substituted. Illustrative carbocyclic aromatic groups described herein include, but are not limited to, phenyl, naphthyl, and the like. Illustrative heterocyclic aromatic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

The term "alkylene" as used herein includes molecular fragments comprising divalent groups that are formed from a linear or branched chain of carbon atoms. Illustrative examples include methylene, 1,2-ethylene, 1-methyl-1,2-ethylene, 1,4-butylene, 2,3-dimethyl-1,4-butylene, 2-methyl-2-ethyl-1,5-pentylene, and the like.

The terms "heteroalkyl" and "heteroalkylene" as used herein include molecular fragments or radicals comprising monovalent and divalent, respectively, groups that are formed from a linear or branched chain of carbon atoms and heteroatoms, wherein the heteroatoms are selected from nitrogen, oxygen, and sulfur, such as alkoxyalkyl, alkyleneoxyalkyl, aminoalkyl, alkylaminoalkyl, alkyleneaminoalkyl, alkylthioalkyl, alkylenethioalkyl, alkoxyalkylaminoalkyl, alkylaminoalkoxyalkyl, alkyleneoxyalkylaminoalkyl, and the like. It is to be understood that neither heteroalkyl nor heteroalkylene includes oxygen-oxygen fragments. It is also to be understood that neither heteroalkyl nor heteroalkylene includes oxygen-sulfur fragments, unless the sulfur is oxidized as S(O) or S(O)2.

The term "cycloalkyl" as used herein refers to a monovalent chain of carbon atoms, a portion of which forms a ring. The term "cycloalkenyl" as used herein refers to a monovalent chain of carbon atoms containing one or more unsaturated bonds, at least a portion of which forms a ring.

The term "heterocycloalkyl" as used herein generally refers to a monovalent chain of carbon atoms and heteroatoms, at least a portion of which forms a ring. The term "heterocycloalkenyl" as used herein refers to a monovalent chain of carbon atoms and heteroatoms containing one or more unsaturated bonds, a portion of which forms a ring, wherein the heteroatoms are selected from nitrogen, oxygen or sulfur.

As used herein, haloalkyl is generally taken to mean an alkyl group wherein one or more hydrogen atoms is replaced with a halogen atom, independently selected in each instance from the group consisting of fluorine, chlorine, bromine and iodine. Non-limiting, illustrative examples include, difluoromethly, 2,2,2-trifluoroethyl, 2-chlorobutyl, 2-chloro-2-propyl, trifluoromethyl, bromodifluoromethyl, and the like.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), and the like, or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Stereosel. Biocatal., 775-797, (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, arylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$)alkoxy, each of which is optionally further substituted with one or more of 1 to 3 halogen atoms; optionally substituted aryl($C_2$-$C_{16}$)alkanoyl, such as the aryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess therapeutically effective biological activity in the amount administered, but instead undergo one or more spontaneous chemical reaction(s), enzyme-catalyzed chemical reaction(s), and/or metabolic chemical reaction(s), and the like, or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

As used herein, the term "optionally substituted" includes a wide variety of groups that replace one or more hydrogens on a carbon, nitrogen, oxygen, or sulfur atom, including monovalent and divalent groups. Illustratively, optional substitution of carbon includes, but is not limited to, halo, hydroxy, alkyl, alkoxy, haloalkyl, haloalkoxy, aryl, arylalkyl, acyl, acyloxy, and the like. In one aspect, optional substitution of aryl carbon includes, but is not limited to, halo, amino, hydroxy, alkyl, alkenyl, alkoxy, arylalkyl, arylalkyloxy, hydroxyalkyl, hydroxyalkenyl, alkylene dioxy, aminoalkyl, where the amino group may also be substituted with one or two alkyl groups, arylalkyl groups, and/or acylgroups, nitro, acyl and derivatives thereof such as oximes, hydrazones, and the like, cyano, alkylsulfonyl, alkylsulfonylamino, and the like. Illustratively, optional substitution of nitrogen, oxygen, and sulfur includes, but is not limited to, alkyl, haloalkyl, aryl, arylalkyl, acyl, and the like, as well as protecting groups, such as alkyl, ether, ester, and acyl protecting groups, and pro-drug groups. Illustrative protecting groups contemplated herein are described in Greene & Wuts "Greene's protective groups in organic synthesis," 4th Ed., John Wiley & Sons, (NY, 2006). It is further understood that each of the foregoing optional substituents may themselves be additionally optionally substituted, such as with halo, hydroxy, alkyl, alkoxy, haloalkyl, haloalkoxy, and the like.

References to therapeutically acceptable salts include acid addition salts. Illustrative acid addition salts include but are not limited to, those formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

References to therapeutically acceptable salts include base salts. Illustrative base salts include but are not limited to, those formed from bases which form non-toxic salts. Illustrative examples include the aluminium, arginine, benzathine, calcium, choline, diethylamine, diolamine, glycine, lysine, magnesium, meglumine, olamine, potassium, sodium, tromethamine and zinc salts.

In both the instance of acid addition salts and base salts, such salts may be hemisalts. Illustrative hemisalts of acids and bases, include but are not limited to, those formed from, for example, hemisulphate and hemicalcium salts.

The following illustrative examples of the compounds are described.

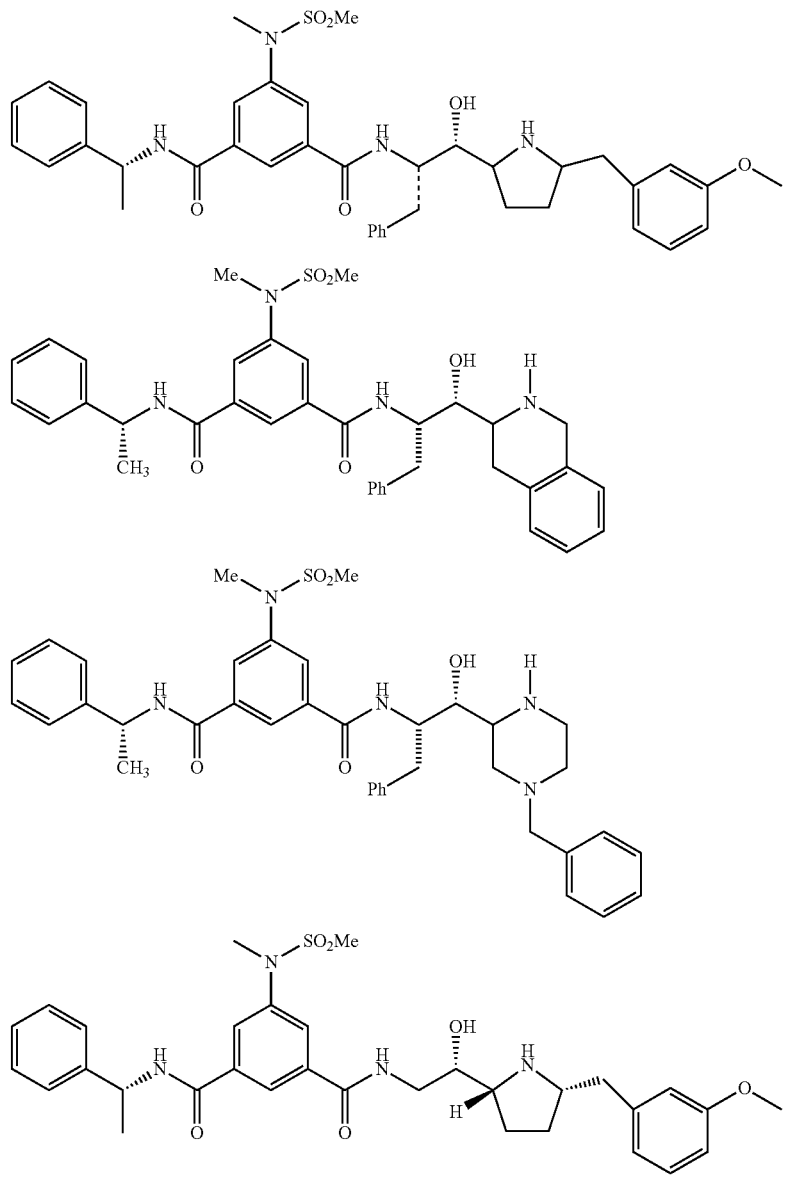

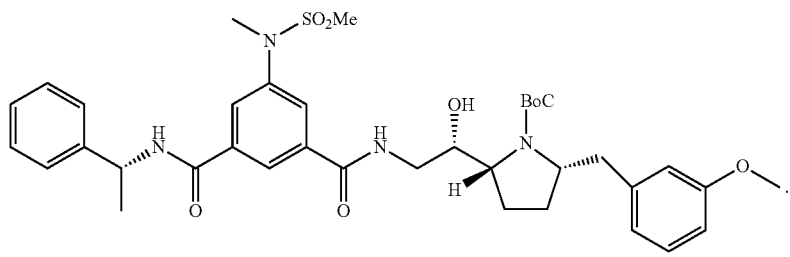
In another illustrative embodiment, the following illustrative examples of the compounds are described
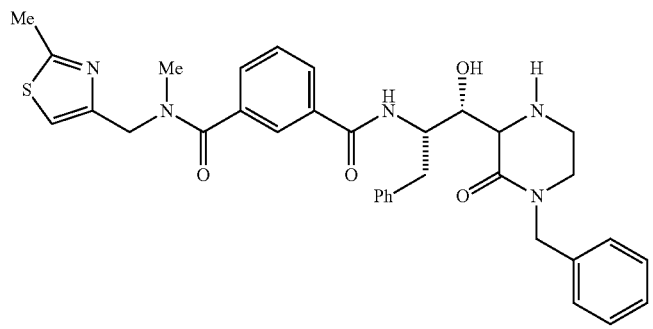
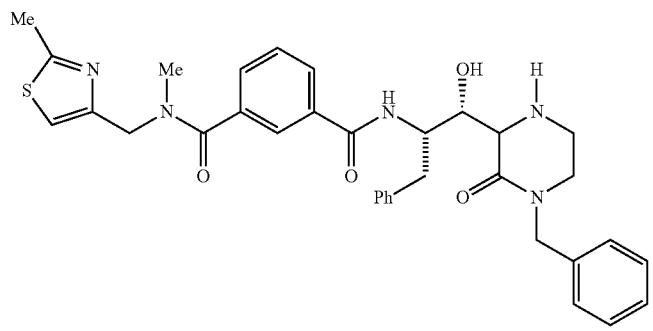
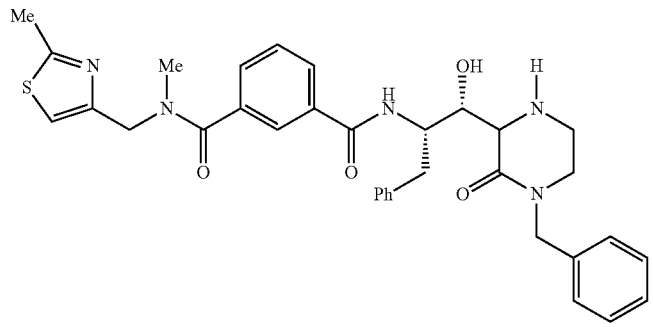
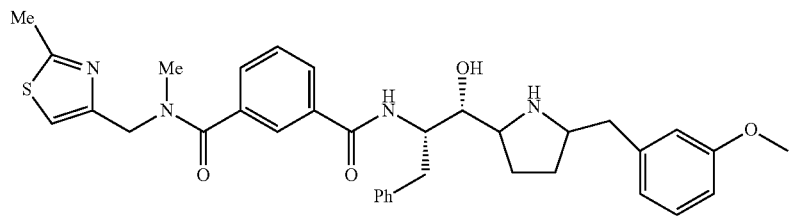

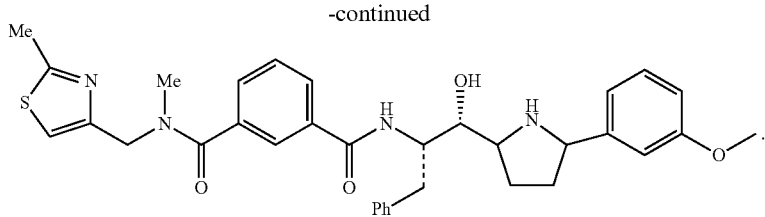

In another illustrative embodiment, the following illustrative examples of the compounds are described

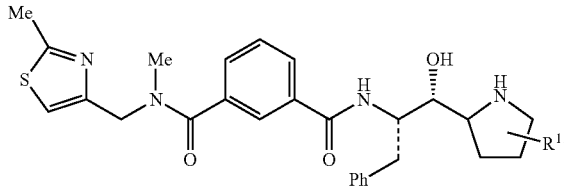

where R[11]=alkyl, heteroalkyl, optionally substituted aryl, oxyalkyl, aminoalkyl, thioalkyl;

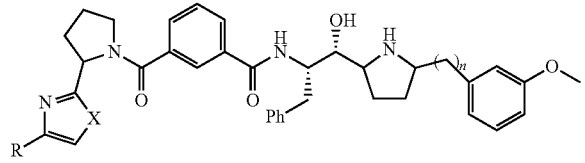

where X=O, S, NMe; R=alkyl, heteroalkyl; n is 0 to 4; and

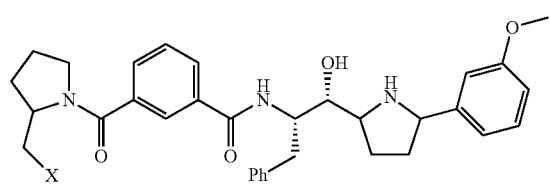

where X=OR, NHR, alkyl, hydroxyalkyl, heteroalkyl.

In another illustrative embodiment, the following illustrative examples of the compounds are described

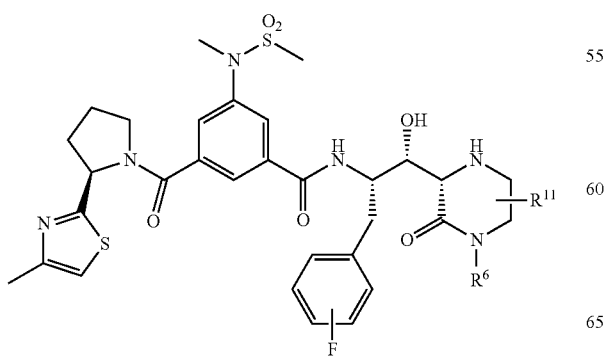

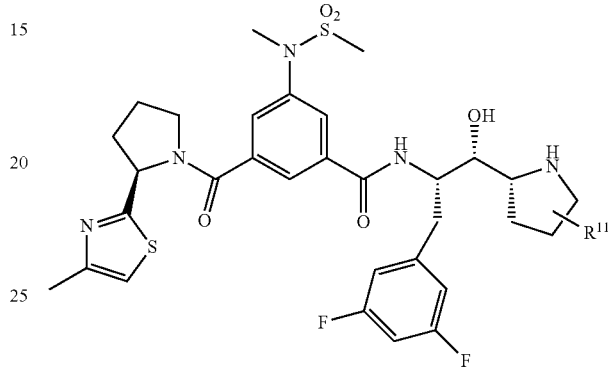

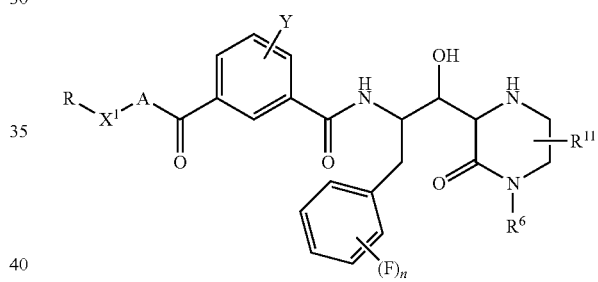

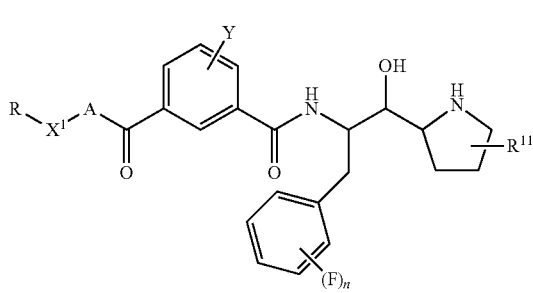

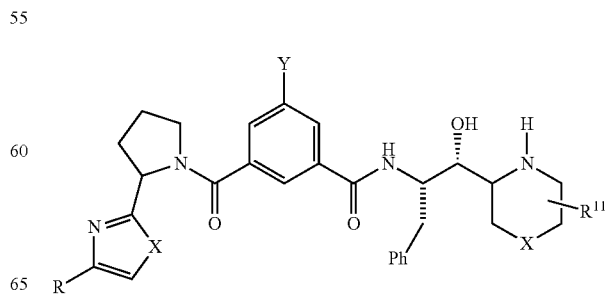

-continued

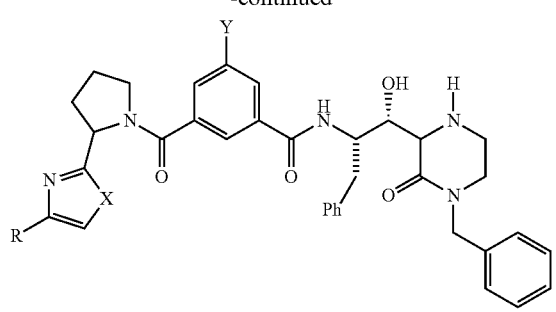

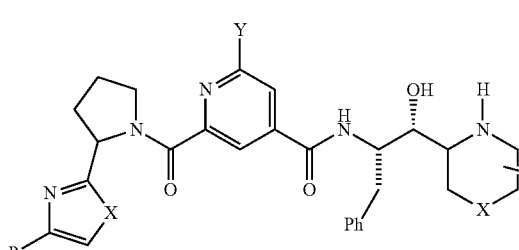

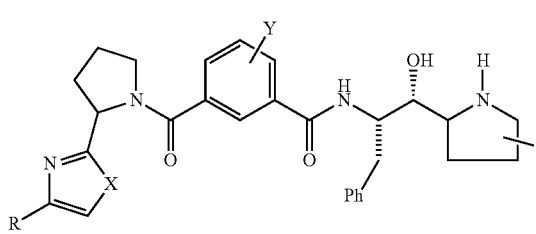

where X=O, S, NMe; N-alkyl, R=alkyl, heteroalkyl; Y=hydrogen, alkyl, oxyalkyl, aminoalkyl, NRSO₂R', NRCOR', NRCO₂R'; and $R^{11}$ is independently in each instance hydrogen, alkyl, heteroalkyl, aryl, heteroaryl, (hetero)arylalkyl, oxyalkyl, aminoalkyl, thioalkyl.

In another illustrative embodiment, the following illustrative examples of the compounds are described

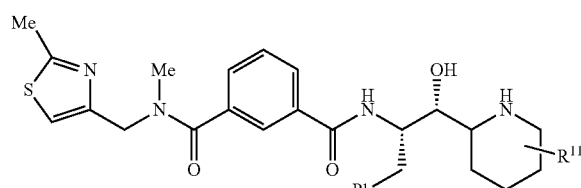

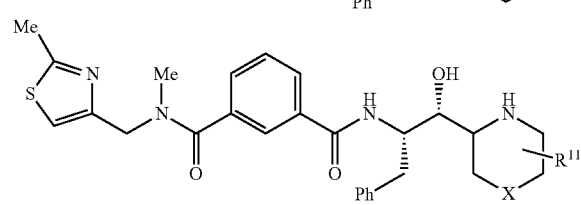

where $R^{11}$=alkyl, heteroalkyl, optionally substituted aryl, oxyalkyl, aminoalkyl, thioalkyl; and X=O, S, NMe, N-alkyl, or N-arylalkyl.

In another illustrative embodiment, the following non-limiting examples are described:

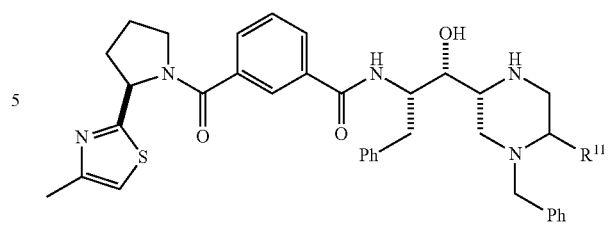

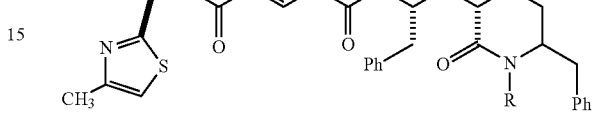

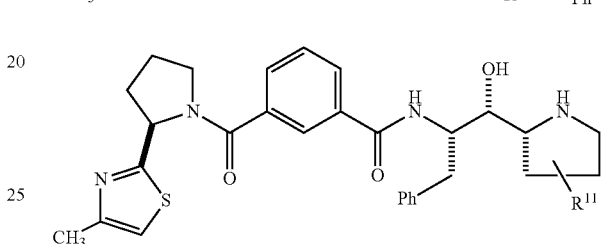

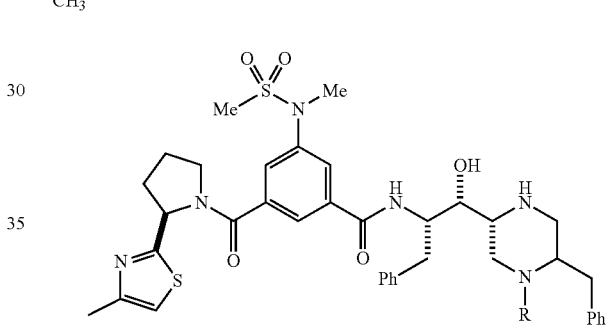

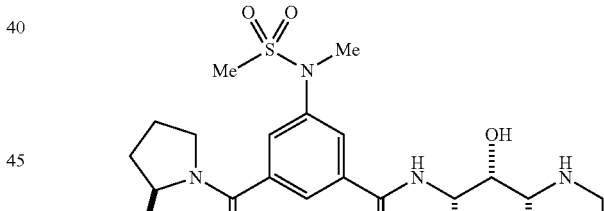

where R is H or alkyl; and $R^{11}$ is hydrogen, alkyl, aryl, alkylaryl, heteroalkyl, heteroaryl. In another embodiment, $R^{11}$ is hydrogen, alkyl, arylalkyl

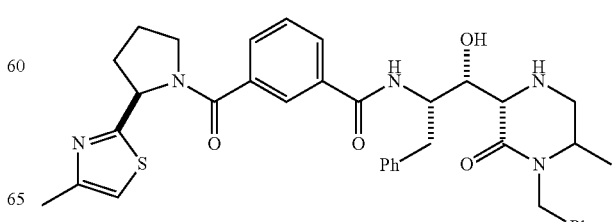

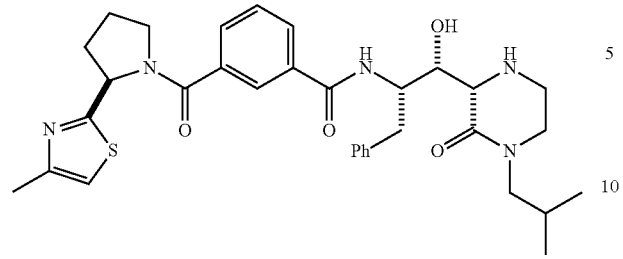
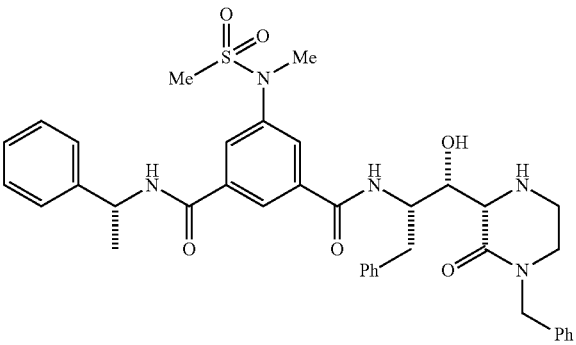
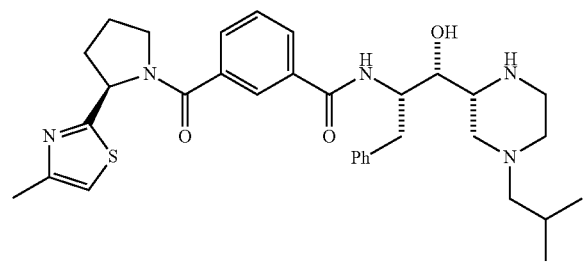
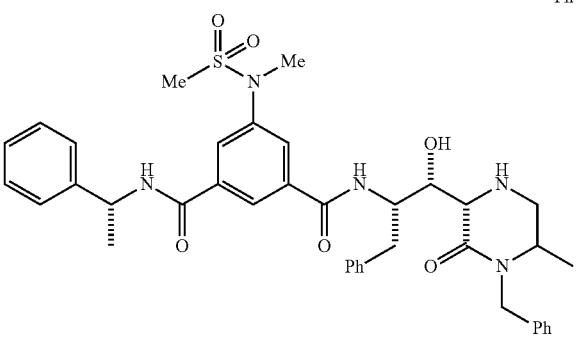
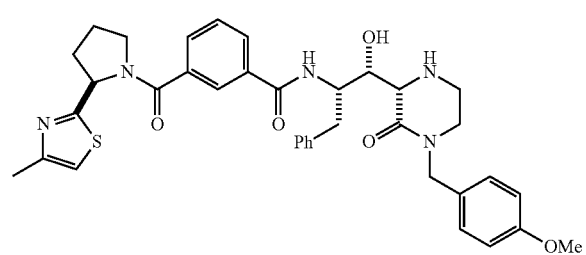
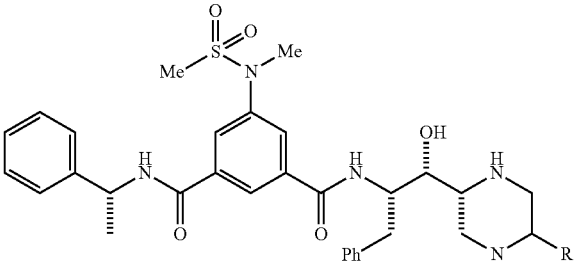
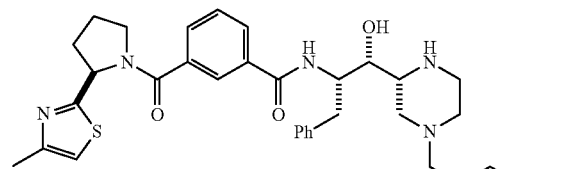
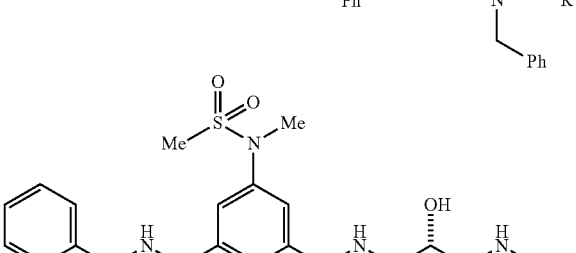
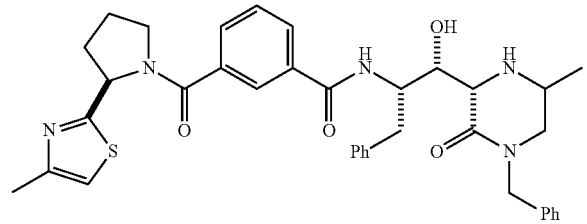
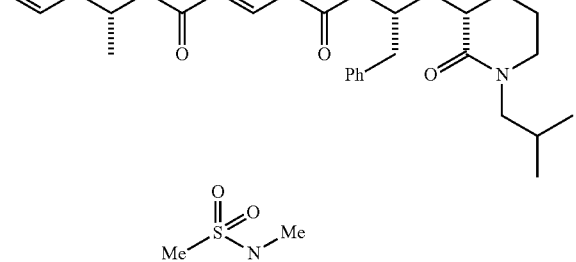
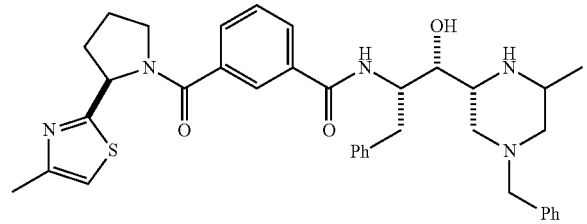
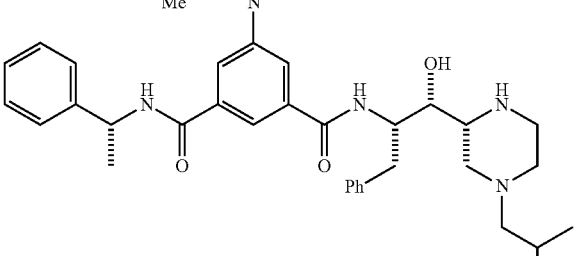
In another illustrative embodiment, the following non-limiting examples are described:

27
-continued
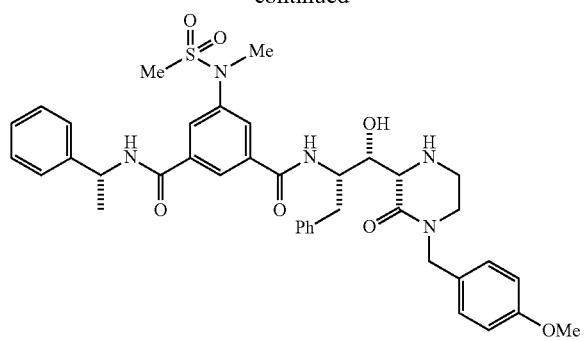
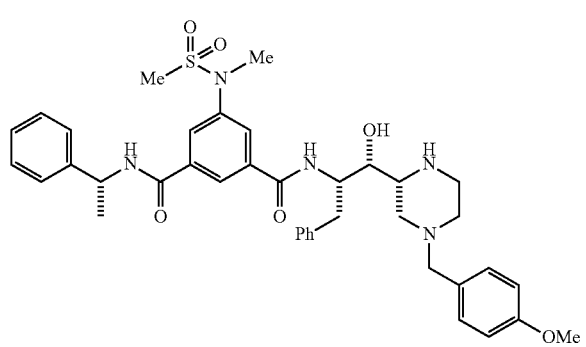
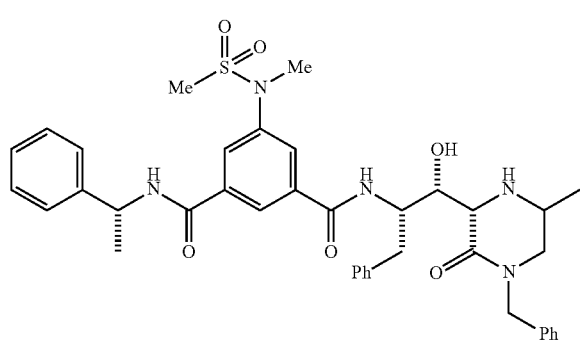
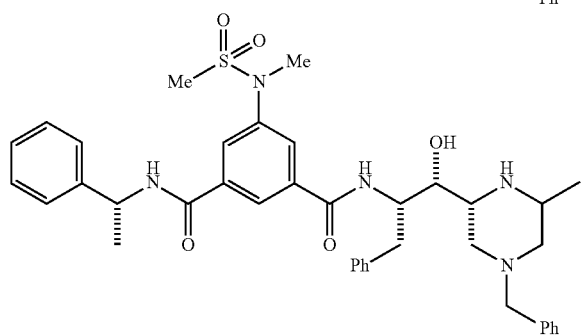
R = H, alkyl
28
-continued
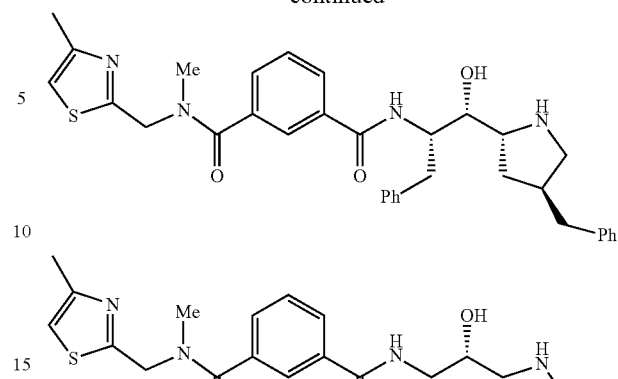
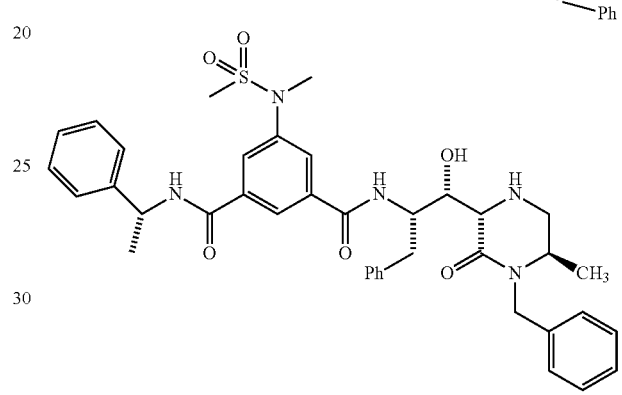
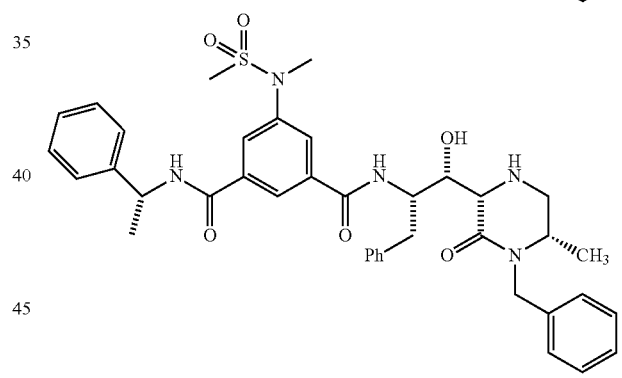
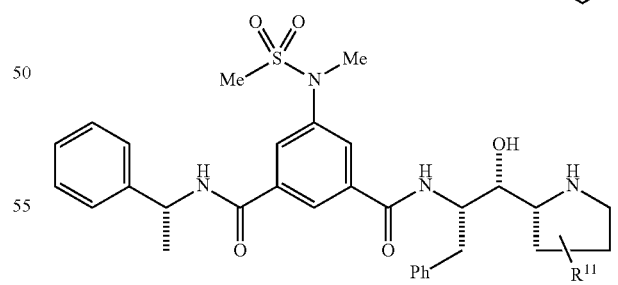
where $R^{11}$ is H, alkyl, aryl, alkylaryl, heteroalkyl, or heteroaryl.
In each of the foregoing embodiments, the compounds may be prepared using conventional synthetic processes, and/or processes as described herein. In one embodiment, compounds described herein can be prepared by the process shown in the following scheme.

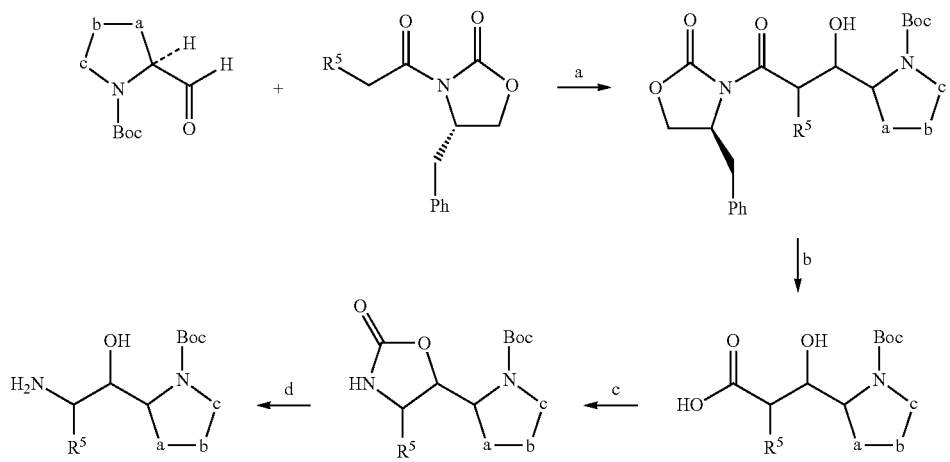

a) n-Bu$_2$BOTf, i-Pr$_2$NEt, CH$_2$Cl$_2$, −78° C. to RT; b) LiOH.H$_2$O, H$_2$O$_2$, THF/H$_2$O, 0° C.; c) DPPA, Et$_3$N, toluene, 80° C., RT; d) 1N aq. LiOH, EtOH, 85° C.

In other embodiments, the compounds described herein can be prepared by the process shown in one of the following schemes (a) EDC, HOBt, DIPEA, DMF—CH$_2$Cl$_2$).

In another embodiment, compounds described herein can be prepared from an intermediate compound prepared by the process shown in the following scheme.

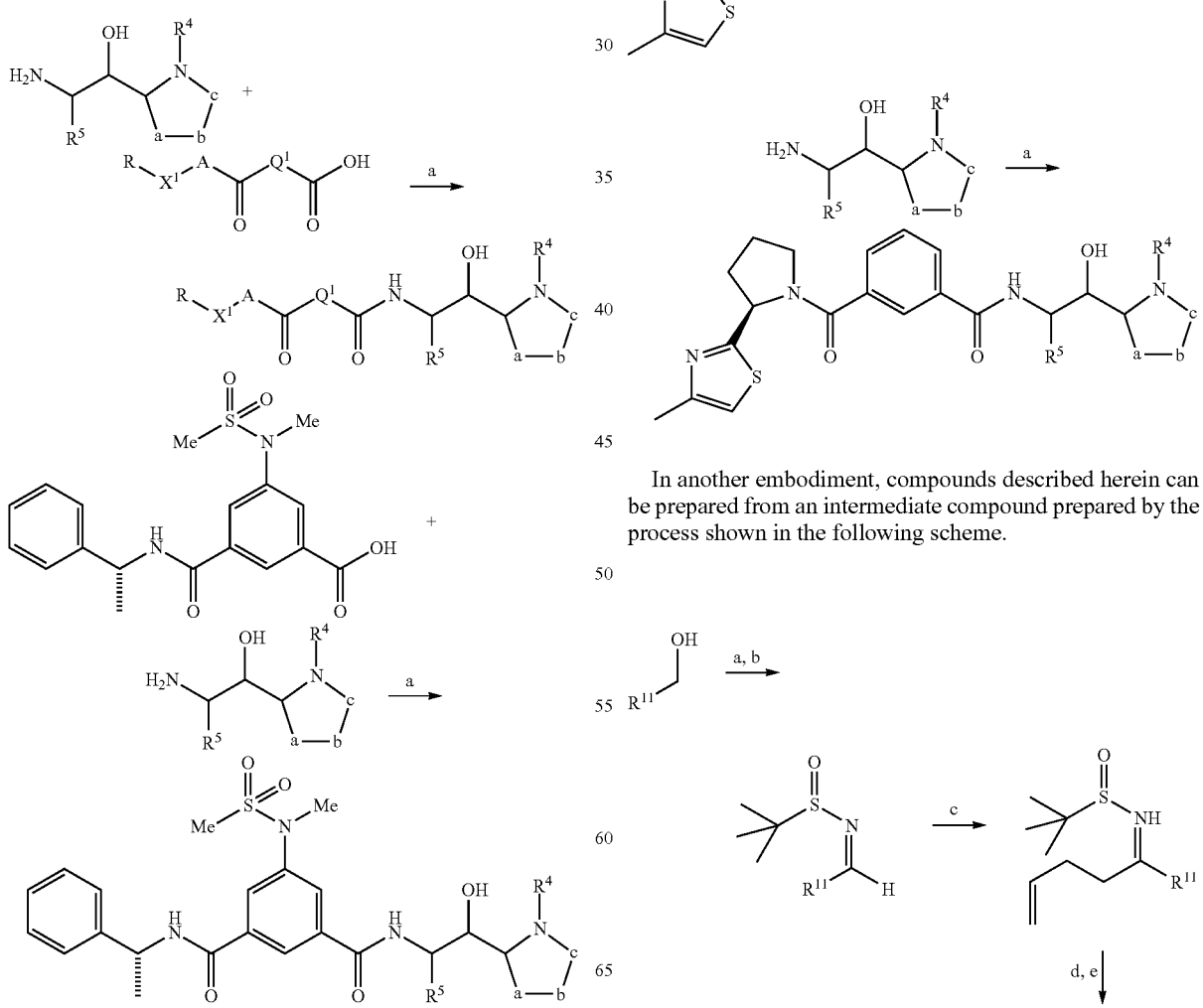

31

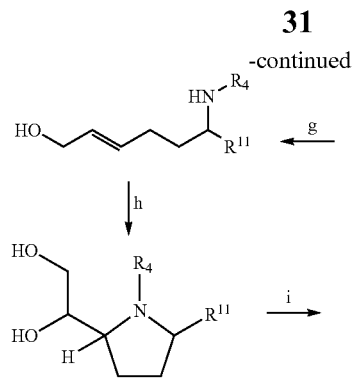

32

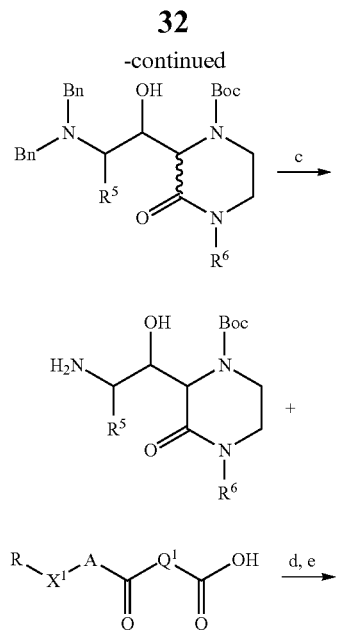

a) Dess-Martin, NaHCO3; b) tert-butylsulfinamide, Ti(OEt)$_4$; c) 4-pentenyl magnesium bromide, DCM, 0° C.; d) 6N HCl(aq), MeOH, 40° C.; e) $R^4$-LG; f) allyl acetate, Grubbs' cat. (II), DCM, reflux; g) K$_2$CO$_3$, MeOH, RT; h) Ti(O-i-Pr)$_4$, (L)-(+)-DIPT, 4 Å molecular sieves, −20° C.; i) NaIO$_4$; MeOH/H$_2$O(2/1), RT.

In another embodiment, compounds described herein can be prepared by the process shown in the following scheme.

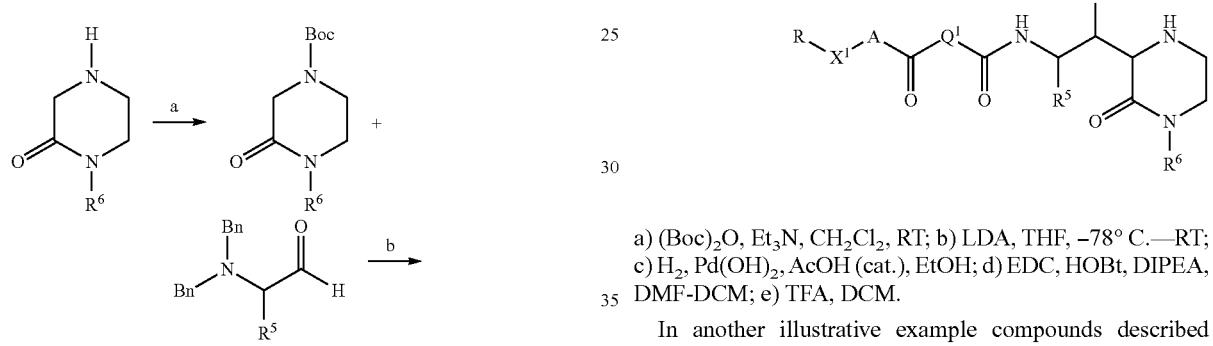

a) (Boc)$_2$O, Et$_3$N, CH$_2$Cl$_2$, RT; b) LDA, THF, −78° C.—RT; c) H$_2$, Pd(OH)$_2$, AcOH (cat.), EtOH; d) EDC, HOBt, DIPEA, DMF-DCM; e) TFA, DCM.

In another illustrative example compounds described herein are prepared as shown in the following scheme.

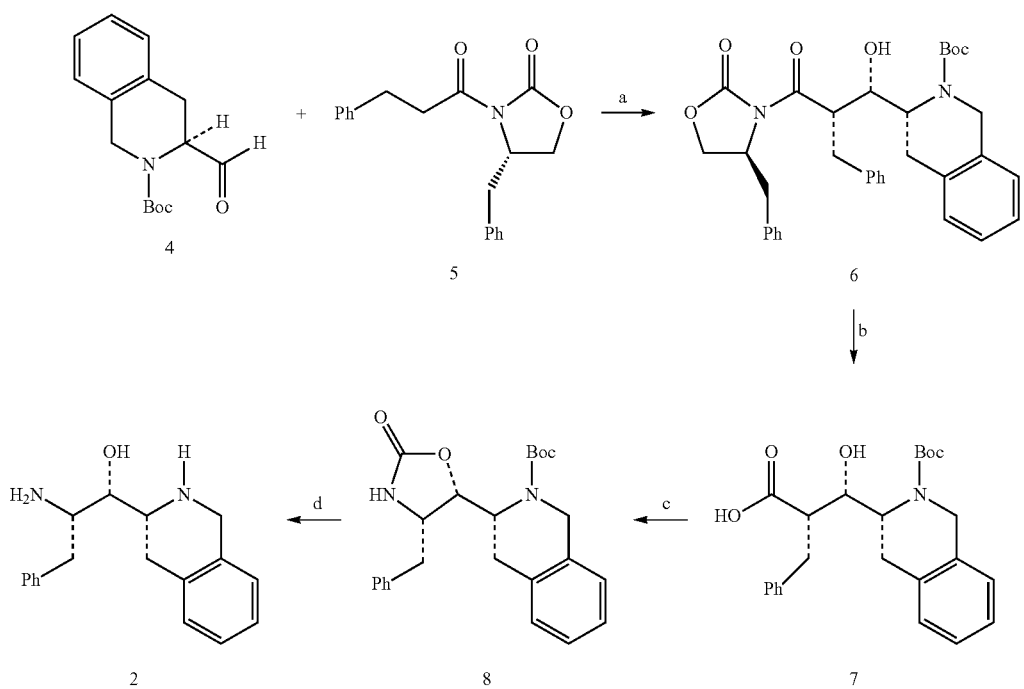

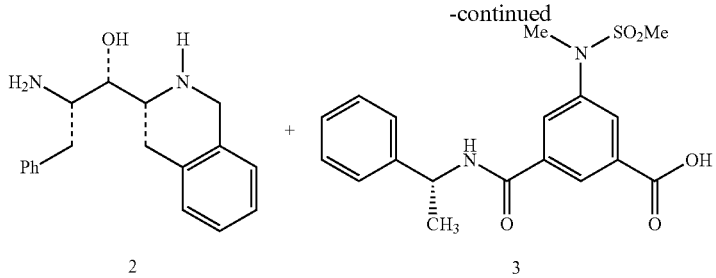

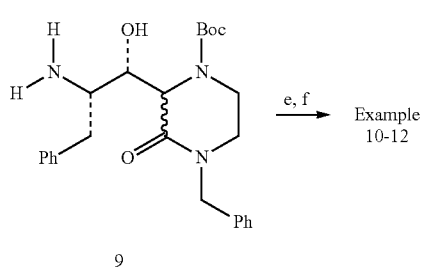

a) n-Bu₂BOTf, i-Pr₂NEt, CH₂Cl₂, −78° C. to RT; b) LiOH.H₂O, H₂O₂, THF/H₂O, 0° C.; c) DPPA, Et₃N, toluene, 80° C., RT; d) 1N aq. LiOH, EtOH, 85° C.; e) EDC, HOBt, i-Pr₂Net, DMF—CH₂Cl₂ RT.

As shown above, the amine 2 was synthesized from N-Boc-L-1,2,3,4-tetrahydroisoquinoline-3-carboxaldehyde 4 based upon a reported procedure (WO 2005/016876 and Ghosh, A. K.; Hussain, K. A.; Fidanze, S. *J. Org. Chem.* 1997, 62, 6080-6082). Described herein is the use of (S)-4-benzyl-2-oxazolidinone in place of the previously described use of (S)-(−)-4-isopropyl-2-oxazolidinone.

In another illustrative example compounds described herein are prepared as shown in the following scheme.

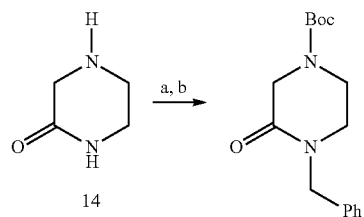

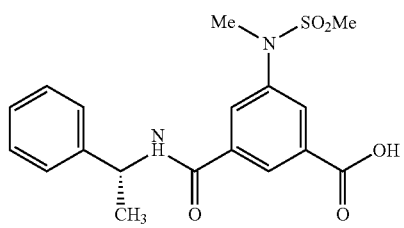

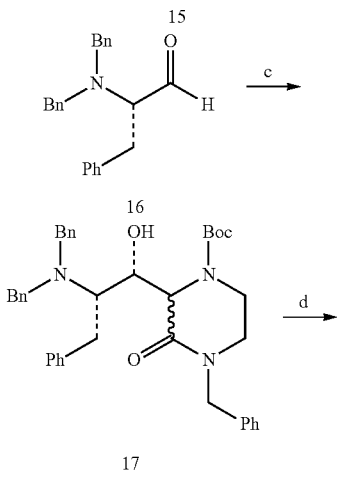

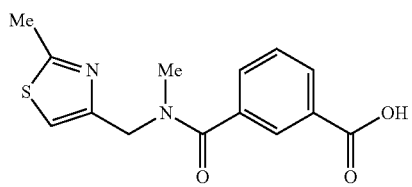

a) (Boc)₂/ Et₃N, CH₂Cl₂, RT; b) NaH, BnBr, DMF, 90° C.; c) LDA, THF, −78° C. to RT; d) H₂, Pd(OH)₂, AcOH (cat.), EtOH; e) Acid (18a-c), EDC/HOBt, DIPEA, DMF—CH₂Cl₂, acid 18a or 18b; f) TFA/CH₂Cl₂.

In another illustrative example compounds described herein are prepared as shown in the following scheme.

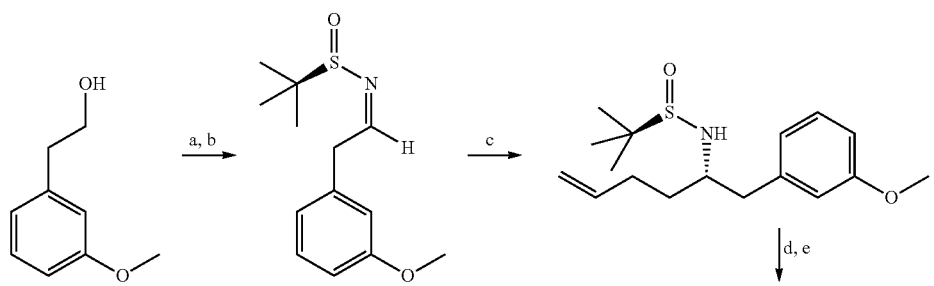

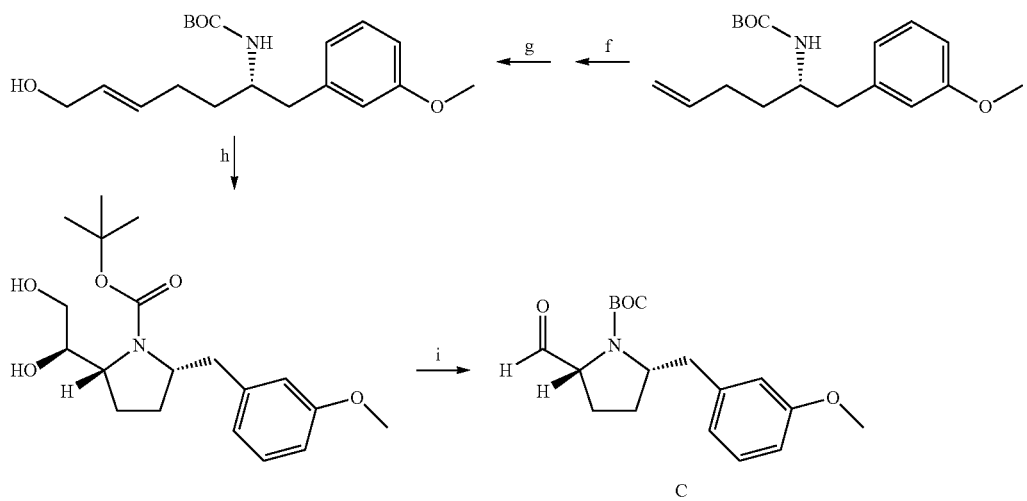
a) Dess-Martin, NaHCO₃; b) tert-butylsulfinamide, Ti(OEt)₄; c) 4-pentenyl magnesium bromide, DCM, 0° C.; d) 6N HCl (aq), MeOH, 40° C.; e) (Boc)₂O, THF, RT; f) allyl acetate, Grubbs' cat. (II), DCM, reflux; g) K₂CO₃, MeOH, RT; h) Ti(O-i-Pr)₄, (L)-(+)-DIPT, 4 Å molecular sieves, −20° C.; i) NaIO₄; MeOH/H₂O(2/1), RT.
In another illustrative example compounds described herein are prepared as shown in the following scheme.
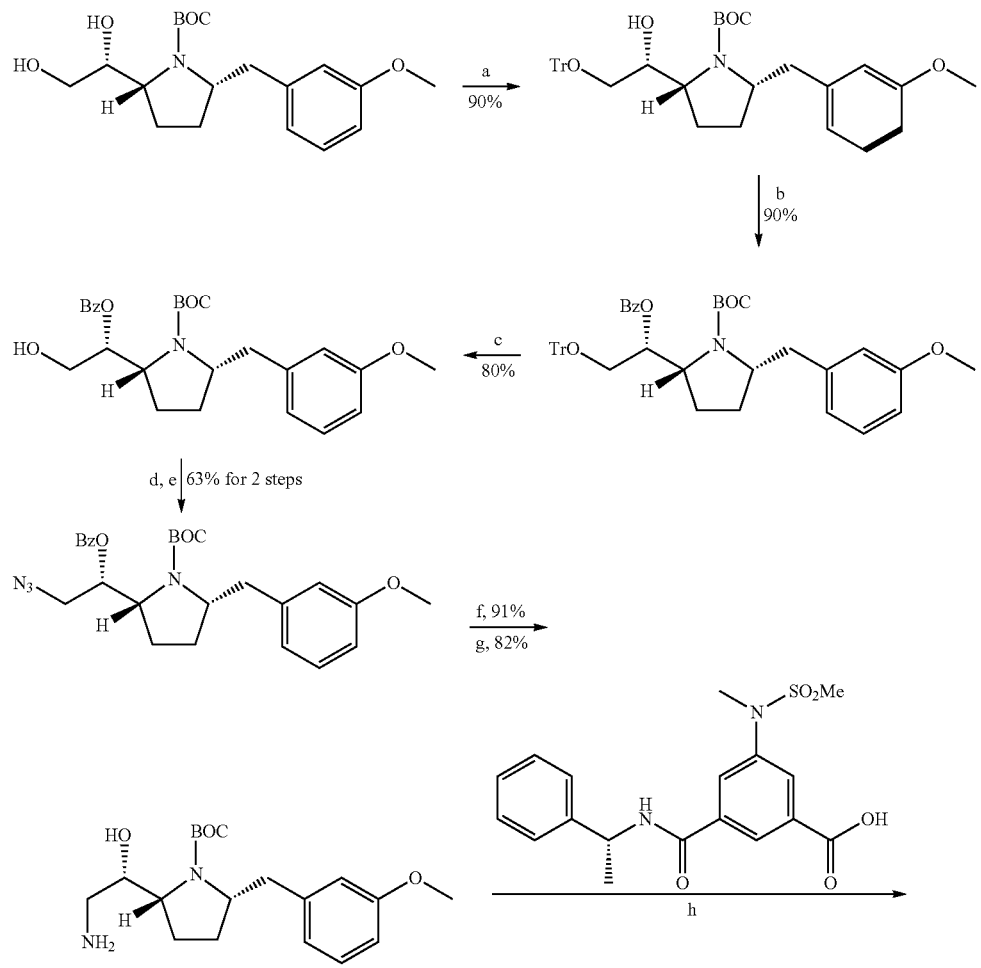

-continued

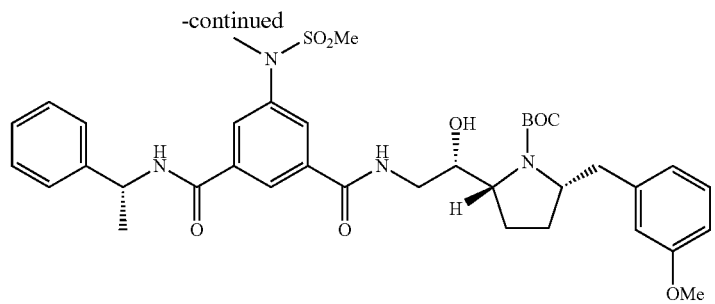

Inhibitor A

↓ i

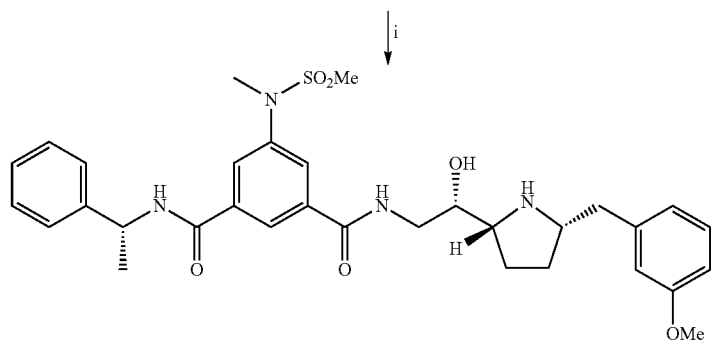

Inhibitor B a) TritylCl, DMAP, Et$_3$N, DCM, RT; b) PhCOCl, DMAP, Et$_3$N, DCM, RT; c) TsOH, MeOH, RT; d) MsCl, DMAP, Et$_3$N, DCM, RT; e) NaN$_3$, 18-crown-6-ether, DMF, 80° C.; f) Cs$_2$CO$_3$, MeOH, RT; g) 10% Pd—C, H$_2$, EtOAc, RT; h) EDC, HOBt, THF, RT; i) TFA, DCM.

In certain embodiments, the starting materials or intermediate compounds may contain additional functional groups. It is appreciated that protecting groups for such functional groups may be required in one or more of the steps in the schemes shown above. Illustrative examples of protecting groups appear in Greene's Protective Groups in Organic Synthesis, 4th Edition, Peter G. M. Wuts and Theodora W. Greene, John Wiley & Sons, Inc., 2006.

In another embodiment, a method of treating a patient in need of relief from

Alzheimer's disease, the method comprising the step of administering to the patient a therapeutically effective amount of a composition comprising the compound of any one of the preceding embodiments is described.

As used herein, treatment is meant to include prevention, amelioration, alleviation, or elimination of one or more symptoms of Alzheimer's disease, including but not limited to cognitive dysfunction, memory dysfunction, and behavioral disturbances.

In other embodiments, the compounds described herein can be prepared and administered in a wide variety of oral, parenteral, and topical dosage forms. See generally, Remington: The Science and Practice of Pharmacy, (21$^{st}$ ed., 2005). Thus, the compounds described herein can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds described herein can be administered transdermally. It is also envisioned that multiple routes of administration (e.g., intramuscular, oral, transdermal) can be used to administer the compounds described herein. Accordingly, in various embodiments, pharmaceutical compositions comprising a pharmaceutically acceptable carrier or excipient and one or more compounds of the invention are described.

The pharmaceutical compositions containing one or more of the compounds described herein may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Formulations for oral use include tablets which contain the active ingredient in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, maize starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example, peanut oil, liquid paraffin, or olive oil.

Aqueous suspensions can include pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g, heptadecaethylene-oxycetanol, or condensation products of ethylene exide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monooleate. The aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

Oily suspensions may be formulated by suspending the active ingredient in a vegetable oil, for example, arachis oil, olive oil, sesame oil, or coconut oil, or in a mineral oil such as liquid paraffin. The oily suspensions may contain a thickening agent, for example, beeswax, hard paraffin, or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the compounds described herein may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate. The emulsions may also contain sweetening and flavoring agents.

Syrups and elixirs may be formulated with sweetening agents, for example glycerol, sorbitol, or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may be a sterile injectable solution or suspension in a non-toxic parenterally-acceptable diluent or solvent. Among the acceptable vehicles and solvents that may be employed are water, 1,3-butanediol, Ringer's solution and isotonic sodium chloride solution. In addition, sterile fixed oils are conventionally employed as a solvent or suspending medium. For this purpose any bland fixed oil may be employed including synthetic mono- or diglycerides. Fatty acids such as oleic acid also find use in the preparation of injectibles.

The compounds described herein may contain one or more chiral centers, or may otherwise be capable of existing as multiple stereoisomers. The scope of the present invention includes pure stereoisomers as well as mixtures of stereoisomers, such as enantiomers, diastereomers, and enantiomerically or diastereomerically enriched mixtures. The compounds described herein may be capable of existing as geometric isomers. The scope of the present invention includes pure geometric isomers or mixtures of geometric isomers.

In another embodiment, compounds described herein are useful in methods for decreasing memapsin 2 activity, decreasing hydrolysis of a β-secretase site of a memapsin 2 substrate, and/or decreasing the accumulation of β-amyloid protein relative to the amount of memapsin 2 activity, hydrolysis of a β-secretase site, and accumulation of β-amyloid protein, respectively, in the absence of the β-secretase inhibitor.

Additional features of the present invention will become apparent to those skilled in the art upon consideration of the following description of illustrative exemplified embodiments for carrying out the invention. While certain embodiments of the present invention have been described and/or exemplified herein, it is contemplated that considerable variation and modification thereof are possible. Accordingly, the present invention is not limited to the particular embodiments described and/or exemplified herein.

EXAMPLES

Compound Examples (S)-2-(dibenzylamino)-3-phenylpropanal was synthesized via a Swern oxidation reaction from the corresponding alcohol according to a literature procedure (O'Brien, P., et al., J. Org. Chem. 2002, 67, 304).

Synthesis of Inhibitor GRL-0849AL. Step A—Tert-butyl-4-isobutyl-3-oxopiperazine-1-carboxylate. Tert-butyl-3-oxopiperazine-1-carboxylate (300 mg, 1.49 mmol) was dissolved in anhydrous DMF (5.00 mL) and the solution was cooled to 0° C. Sodium hydride (60% in mineral oil—120 mg, 3.00 mmol) was added to the solution which was stirred at 0° C. for 5 min and allowed to warm to room temperature for 2 h. 1-iodo-2-methylpropane (0.35 mL, 3 mmol) was added to the solution and the mixture was stirred at room temperature for 12 h. The reaction was cooled to 0° C. and quenched with cold water. The solution was diluted with EtOAc and washed with $H_2O$ two or three times. The organic phase was dried over $Na_2SO_4$, filtered and concentrated under reduced pressure. The crude mixture was purified on silica gel using a gradient of hexane to hexane:EtOAc (5:1) to afford 3 as a white fluffy solid (180 mg, 46% Yield).

Step 2—(S)-Tert-butyl-2-((1S,2S)-2-(dibenzylamino)-1-hydroxy-3-phenylpropyl)-4-isobutyl-3-oxopiperazine-1-carboxylate. Tert-butyl-4-isobutyl-3-oxopiperazine-1-carboxylate (155 mg, 0.6 mmol) was dissolved in anhydrous THF (3 mL) and the solution was cooled to −78° C. LHMDS (1.0 M in THF—1.21 mL, 1.21 mmol) was added dropwise and the mixture was stirred at −78° C. for 2 h. A solution of (S)-2-(dibenzylamino)-3-phenylpropanal (200 mg, 0.61 mmol) in 2 mL of THF was added dropwise to the reaction and the mixture was stirred at −78° C. for 1 h. The reaction was quenched by slow addition of $H_2O$ and allowed to warm to room temperature. The solution was diluted with EtOAc and washed with $H_2O$ 2 to 3 times. The organic phase was dried over $Na_2SO_4$, filtered and concentrated on the rotovap.

The crude mixture was purified on silica gel using a gradient of hexane to hexane:EtOAc (20:1) to afford 4 as an off-white solid (102 mg, 29% yield).

Step 3—(S)-tert-butyl-2-((1S,2S)-2-(dibenzylamino)-1-hydroxy-3-phenylpropyl)-4-isobutyl-3-oxopiperazine-1-carboxylate (98.8 mg, 0.17 mmol) was dissolved in absolute ethanol (10 mL). Pearlman's catalyst (20% w/w, 35 mg) and glacial acetic acid (0.02 mL, 0.34 mmol) were added to the solution and the mixture was stirred under a hydrogen stream at 1 atm for 12 h. The solution was filtered through a pad of celite and the solvent was removed under vacuum. The crude mixture was purified on silica gel using a gradient of DCM to DCM:MeOH (19:1) to afford the didebenzylated amine as a light brown solid (62 mg, 94% yield).

Step 4—The mono N—(R)-pheneth-1-yl amide of 5-(N-methylmethylsulfonamido)-isophthalic acid (Ghosh, A. K. et al, *J. Med. Chem.* 2007, 50, 2399) (60 mg, 0.16 mmol) and the amine derived from step 3 (64.6 mg, 0.16 mmol) were dissolved in anhydrous $CH_2Cl_2$ (3 mL) and the solution was cooled to 0° C. $HOBt.H_2O$ (36.6 mg, 0.24 mmol), EDC.HCl (45.8 mg, 0.24 mmol) and DIPEA (0.167 mL, 0.96 mmol) were added successively and the reaction mixture was stirred at room temperature for 36 h. The solution was diluted with EtOAc and washed with $H_2O$ 2 to 3 times. The organic phase was dried over $Na_2SO_4$, filtered and concentrated on the rotovap. The crude mixture was purified on silica gel using a gradient of hexane to hexane:EtOAc (1:3) to afford the diamide as a white solid (73 mg, 60% yield).

Step 5—The Boc-protected diamide prepared in Step 4 (70 mg, 0.09 mmol) was dissolved in a 3N solution of HCl in EtOAc (4 mL) and the reaction mixture was stirred at room temperature for 2 h. The solvent was removed under vacuum and the crude mixture was dissolved in a 1:1 mixture of THF and saturated $NaHCO_3$ (2 mL); after stirring for 1 h, the THF was removed and the product was extracted with EtOAc (4×2 mL). The organic phase was dried over $Na_2SO_4$, filtered and concentrated on the rotovap. The crude mixture was purified on silica gel using a gradient of DCM to DCM:MeOH (19:1) to afford inhibitor GRL-0849AL as a white solid (54.7 mg, 90 yield). $^1$H NMR (400 MHz, $CDCl_3$) δ 7.99 (s, 1H), 7.95 (s, 1H), 7.87 (s, 1H), 7.53 (d, 1H, J=8.6 Hz), 7.39-7.15 (m, 10H), 6.82 (d, 1H, J=7.6 Hz), 5.29 (m, 1H), 4.67 (m, 1H), 4.05 (m, 1H), 3.47 (d, 1H, J=7.00 Hz), 3.34 (bs, 1H), 3.31 (s, 3H), 3.07 (m, 6H), 2.81 (s, 3H), 1.92 (m, 1H), 1.59 (d, 3H, J=6.9 Hz), 0.85 (d, 3H, J=6.8 Hz), 0.82 (d, 3H, J=6.8 Hz).

Synthesis of Inhibitor (GRL-0889AL). Step 1—tert-butyl-4-(4-methoxybenzyl)-3-oxopiperazine-1-carboxylate. Tert-butyl-3-oxopiperazine-1-carboxylate (320 mg, 1.6 mmol) was dissolved in anhydrous DMF (5 mL) and the solution was cooled to 0° C. Sodium hydride (60% in mineral oil—141 mg, 3.5 mmol) was added to the solution which was stirred at 0° C. for 5 min and allowed to warm to room temperature for 2 h. p-Methoxybenzyl chloride (0.43 mL, 2.93 mmol) was added to the solution and the mixture was stirred at room temperature for 12 h. The reaction was cooled to 0° C. and quenched with cold water. The solution was diluted with EtOAc and washed with $H_2O$ 2 to 3 times. The organic phase was dried over $Na_2SO_4$, filtered and concentrated on the rotovap. The crude mixture was purified on silica gel using a gradient of hexane to hexane:EtOAc (5:1) to afford 9 as a white fluffy solid (385 mg, 75% yield).

Step 2—(S)-tert-butyl-2-((1S,2S)-2-(dibenzylamino)-1-hydroxy-3-phenylpropyl)-4-(4-methoxybenzyl)-3-oxopiperazine-1-carboxylate. Tert-butyl-4-(4-methoxybenzyl)-3-oxopiperazine-1-carboxylate 9 (385 mg, 1.2 mmol) was dissolved in anhydrous THF (5 mL) and the solution was cooled to −78° C. LHMDS (1.0 M in THF, 2.4 mL, 2.4 mmol) was added dropwise and the mixture was stirred at −78° C. for 2 h. A solution of (S)-2-(dibenzylamino)-3-phenylpropanal 1 (396 mg, 1.2 mmol) in 2 mL of THF was added dropwise to the reaction and the mixture was stirred at −78° C. for 1 h. The reaction was quenched by slow addition of $H_2O$ and allowed to warm to room temperature. The solution was diluted with EtOAc and washed with $H_2O$ 2 to 3 times. The organic phase was dried over $Na_2SO_4$, filtered and concentrated on the rotovap. The crude mixture was purified on silica gel using a gradient of hexane to hexane:EtOAc (20:1) to afford 10 as a white solid (234 mg, 30% yield).

Step 3—(S)-tert-butyl-2-((1S,2S)-2-(dibenzylamino)-1-hydroxy-3-phenylpropyl)-4-(4-methoxybenzyl)-3-oxopiperazine-1-carboxylate (163 mg, 0.25 mmol) was dissolved in absolute ethanol (10 mL). Pearlman's catalyst (20% w/w, 57 mg) and glacial acetic acid (0.03 mL, 0.50 mmol) were added to the solution and the mixture was stirred under a hydrogen stream at 1 atm for 12 h. The solution was filtered through a pad of celite and the solvent was removed under vacuum. The crude mixture was purified on silica gel using a gradient of DCM to DCM:MeOH (19:1) to afford the amine as an off-white solid (93 mg, 0.198 mmol). Yield: 79%.

Step 4—the mono N—(R)-pheneth-1-yl amide of 5-(N-methylmethylsulfonamido)-isophthalic acid (40 mg, 0.11 mmol) and the free amine of step 3 (50 mg, 0.11 mmol) were dissolved in anhydrous $CH_2Cl_2$ (3 mL) and the solution was cooled to 0° C. $HOBt.H_2O$ (25 mg, 0.16 mmol), EDC.HCl (31 mg, 0.16 mmol) and DIPEA (0.11 mL, 0.64 mmol) were added successively and the reaction mixture was stirred at room temperature for 36 h. The solution was diluted with EtOAc and washed with $H_2O$ 2 to 3 times. The organic phase was dried over $Na_2SO_4$, filtered and concentrated on the rotovap. The crude mixture was purified on Silica gel using a gradient of hexane to hexane:EtOAc (1:3) to afford the diamide as a white solid (39.7 mg, 45% yield).

Step 5—GRL-0889AL. The Boc-protected diamide of step 4 (27 mg, 0.03 mmol) was dissolved in a 3N solution of HCl in EtOAc (4 mL) and the reaction mixture was stirred at room temperature for 2 h. The solvent was removed under vacuum and the crude mixture was dissolved in a 1:1 mixture of THF and saturated $NaHCO_3$ (2 mL); after stirring for 1 h, the THF was removed and the product was extracted with EtOAc (4×2 mL). The organic phase was dried over $Na_2SO_4$, filtered and concentrated on the rotovap. The crude mixture was purified on silica gel using a gradient of DCM to DCM:MeOH (19:1) to afford inhibitor GRL-0889AL as a white solid (18.6 mg, 81% yield). $^1$H NMR (400 MHz, $CDCl_3$) δ 8.00 (s, 1H), 7.95 (s, 1H), 7.89 (s, 1H), 7.55 (d, 1H, J=8.8 Hz), 7.37-7.23 (m, 10H), 7.18 (d, 1H, J=7.3 Hz), 7.11 (d, 2H, J=8.5 Hz), 6.81 (d, 2H, J=8.5 Hz), 5.29 (m, 1H), 4.67 (m, 1H), 4.53 (d, 1H, J=14.4 Hz), 4.13 (m, 2H), 3.77 (s, 3H), 3.53 (d, 1H, J=6.5 Hz), 3.30 (s, 3H), 3.25 (m, 1H), 3.05 (m, 4H), 2.81 (s, 3H), 2.78 (m, 1H), 1.86 (bs, 1H), 1.59 (d, 3H, J=6.9 Hz).

Method Examples

Inhibition of Memapsin 1, Memapsin 2, and Cathepsin D Catalytic Activity. A substrate peptide $H_3N$-ELDLAVEF-WHDR—$CO_2$ (SEQ ID NO:1) (used for inhibition assay of memapsin 2, memapsin 1, and cathepsin D) was dissolved at 2 mg/mL in DMSO and diluted 1:100 in 0.1 M sodium acetate, pH 4.0 just prior to assay. Inhibitor dissolved in DMSO was diluted into 0.1 M sodium acetate, pH 4.0 (1:100 dilution). A 50 μL aliquot of the inhibitor solution in pH 4 buffer was combined with 150 μL of 0.1 M sodium acetate containing 100-200 nM of memapsin 1, memapsin 2, or cathepsin D. Following a pre-incubation at 37° C., the proteolytic assay was initated by addition of 50 μl of the substrate diluted into pH 4 buffer, and incubation continued at 37° C. Aliquots were removed at time intervals, and combined with an equal volume of MALDI-TOF matrix (α-acid in acetone, 20 mg/mL) and immediately spotted in duplicate onto a stainless-steel MALDI sample plate. MALDI-TOF mass spectrometry was performed on a PE Biosystems Voyager DE instrument at the Molecular Biology Resource Center on campus. The instrument was operated at 25,000 accelerating volts in positive mode with a 150 ns delay. Ions with a mass-to-charge ratio (m/z) were detected in the range of 650-2000 atomic mass units. Data were analyzed by the Voyager Data Explorer module to obtain ion intensity data for mass species of substrates and corresponding products in a given mixture. Relative product formation was calculated as the ratio of signal intensity of the product to the sum of signal intensities of both product and the corresponding substrate. Relative product formed per unit time was obtained from non-linear regression analysis of the data representing the initial 15% formation of product using the model:

$$1-e^{-kT}$$

where k was the relative hydrolytic rate constant and T was time in seconds. Alternatively, relative hydrolytic rates were determined using a fluorogenic cleavage assay (Ermolieff, J. et al., Biochemistry, 39: 12450-12456 (2000)). Initial rates from either method were expressed relative to uninhibited controls and the inhibition constant $K_i$ was determined by a non-linear fit to a tight-binding model of competitive inhibition (Bieth, J., Bayer—Symposium V. Proteinase Inhibitors, pp 463-469, Spinger-Varlag, Berlin (1994)). Results are shown in Cellular Aβ $IC_{50}$ Determinations. The potency of compounds against memapsin 2 catalytic activity was determined in a cellular assay of Aβ production. Compounds that successfully penetrate the cell membrane demonstrated their ability to inhibit memapsin 2 catalytic activity in endosomal compartments, thus blocking the production of Aβ. Chinese hamster ovary cells that over-express human APP695 with the London and Swedish mutations were seeded in multi-well plates at 10% confluency. Compounds are dissolved in DMSO to concentrations near 1 mM, and diluted into culture media to a final concentration near 4 μM (final 0.4% DMSO). Compounds were diluted serially and applied to cells in multi-well plates 48 h after seeding. Incubation was continued in 5% $CO_2$ at 37 degrees C. for 24 h. Aliquots were removed and assayed for $Aβ_{40}$ content using a sandwich ELISA (BioSource International). Amount of $Aβ_{40}$ over the range of concentration of compounds, relative to control incubations, were fit to a 4-parameter $IC_{50}$ model.

Inhibition of Memapsin 2. The potencies of compounds were determined by measurement of their inhibition of memapsin 2 catalytic activity toward a fluorescent substrate. Kinetic inhibition experiments were performed using the procedure as described in Ermolieff, et al. Biochemistry 39:12450-12456 (2000), the teachings of which are incorporated hereby in their entirety. Briefly, assays were performed at pH 4, 37° C., by pre-incubation of memapsin 2 enzyme with compound for 20 minutes. Activity measure was initiated by addition of a fluorogenic substrate FS-2 (Bachem Americas, Torrance, Calif.). Fluorescent signal increase over time was measured as a rate of hydrolysis of the peptide substrate. Inhibition of hydrolytic rate was expressed relative to uninhibited controls and fit to a model for tight-binding inhibitors (J. Bieth, in "Proteinase Inhibitors," Bayer Symposium V, 463-469, 1974). Illustrative inhibition constants are shown in TABLE 1.

TABLE 1

| Example | Structure | MW | Activity $K_i$ | Activity $IC_{50}$ |
|---|---|---|---|---|
| 10 | (epimeric mixture) | 697.84 | <10 μM | NT |

TABLE 1-continued

| Example | Structure | MW | Activity K_i | Activity IC_{50} |
|---|---|---|---|---|
| 11a | pure diastereomer 1<br>unknown absolute stereochemistry at * | 611.75 | <1 μM | <10 μM |
| 11b | pure diastereomer 2<br>unknown absolute stereochemistry at * | 611.75 | >10 μM | NT |
| Comparison compound A | 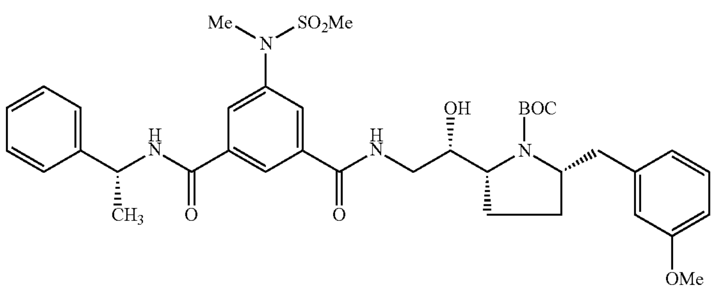 [SMILES: COc1cccc(C[C@@H]2CC[C@H]([C@@H](O)CNC(=O)c3cc(C(=O)N[C@H](C)c4ccccc4)cc(N(C)S(C)(=O)=O)c3)N2C(=O)OC(C)(C)C)c1] | 709.0 | >1 μM | NT |
| Comparison compound B | 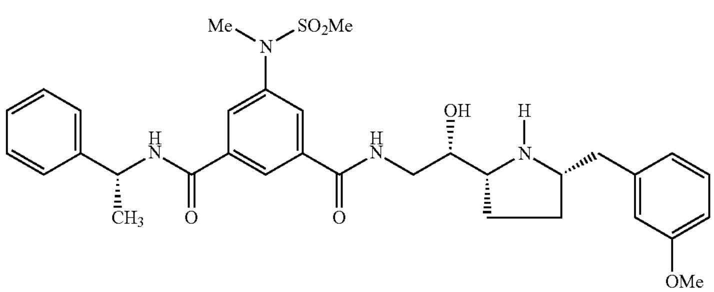 [SMILES: COc1cccc(C[C@@H]2CC[C@H]([C@@H](O)CNC(=O)c3cc(C(=O)N[C@H](C)c4ccccc4)cc(N(C)S(C)(=O)=O)c3)N2)c1] | 608.9 | >10 μM | NT |
| GRL-0299 | 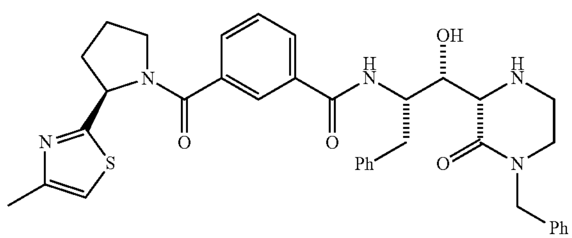 [SMILES: Cc1csc([C@H]2CCCN2C(=O)c2cccc(C(=O)N[C@@H](Cc3ccccc3)[C@H](O)[C@@H]3NCCN(Cc4ccccc4)C3=O)c2)n1] | 637.79 | <1 μM | NT |

TABLE 1-continued

| Example | Structure | MW | Activity $K_i$ | Activity $IC_{50}$ |
|---|---|---|---|---|
| GRL-0619AL | 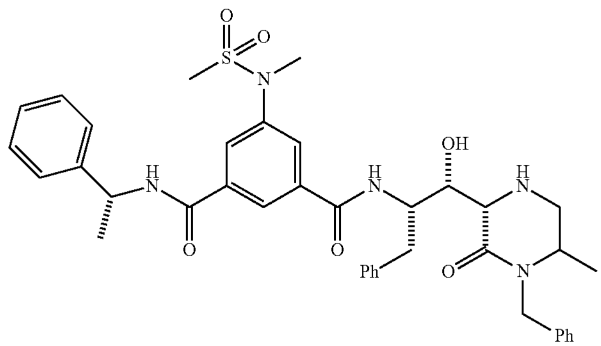 | 711.87 | NT | NT |
| GRL-0669AL | 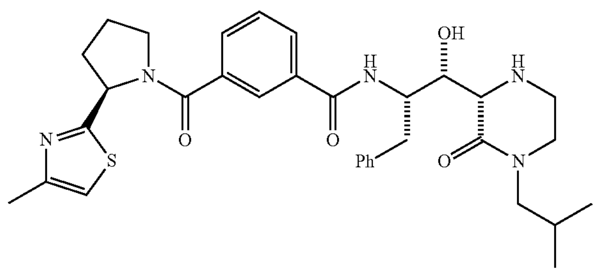 [SMILES: Cc1csc([C@H]2CCCN2C(=O)c2cccc(C(=O)N[C@@H](Cc3ccccc3)[C@H](O)[C@@H]3NCCN(CC(C)C)C3=O)c2)n1] | 603.77 | <1 μM | NT |
| GRL-0819AL | 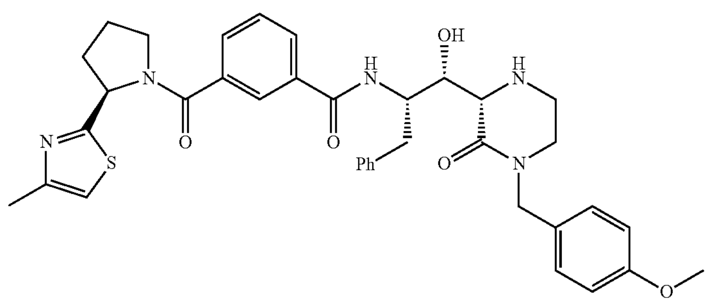 | 667.82 | <1 μM | NT |
| GRL-0849AL | 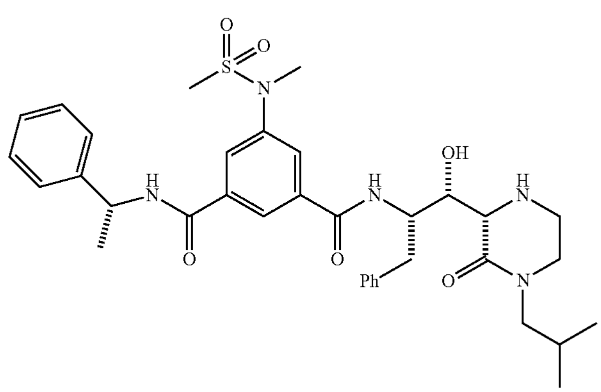 [SMILES: CC(C)CN1CCN[C@@H]([C@@H](O)[C@H](Cc2ccccc2)NC(=O)c2cc(C(=O)N[C@H](C)c3ccccc3)cc(N(C)S(C)(=O)=O)c2)C1=O] | 663.82 | <1 μM | NT |

TABLE 1-continued
| Example | Structure | MW | Activity $K_i$ | Activity $IC_{50}$ |
|---|---|---|---|---|
| GRL-0889AL | 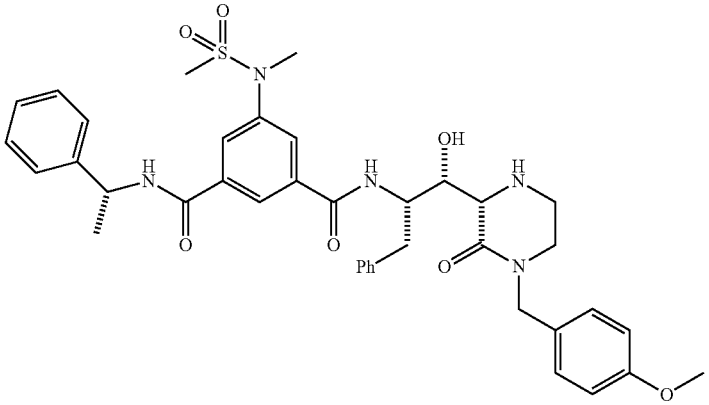 [SMILES: COc1ccc(CN2CCN[C@@H]([C@@H](O)[C@H](Cc3ccccc3)NC(=O)c3cc(C(=O)N[C@H](C)c4ccccc4)cc(N(C)S(C)(=O)=O)c3)C2=O)cc1] | 727.87 | <1 μM | NT |
| GRL-1009AL | 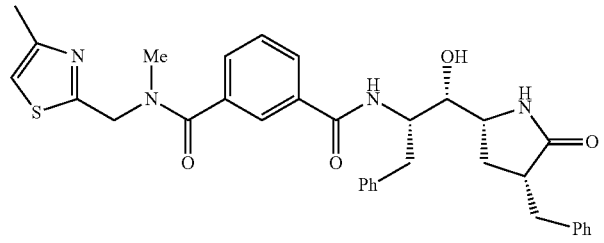 [SMILES: Cc1csc(CN(C)C(=O)c2cccc(C(=O)N[C@@H](Cc3ccccc3)[C@H](O)[C@H]3C[C@@H](Cc4ccccc4)C(=O)N3)c2)n1] | 596.74 | NA | NT |
| GRL-1069AL | 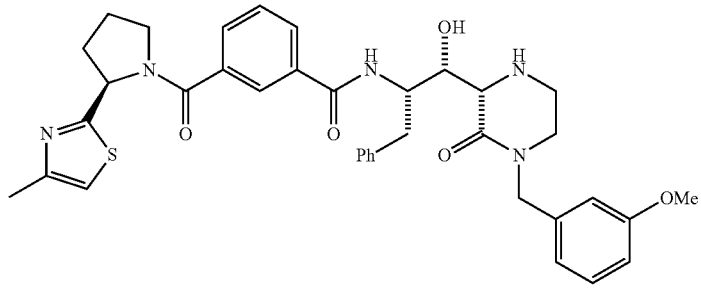 [SMILES: COc1cccc(CN2CCN[C@@H]([C@@H](O)[C@H](Cc3ccccc3)NC(=O)c3cccc(C(=O)N4CCC[C@@H]4c4nc(C)cs4)c3)C2=O)c1] | 667.82 | <1 μM | NT |
| GRL-1079AL | 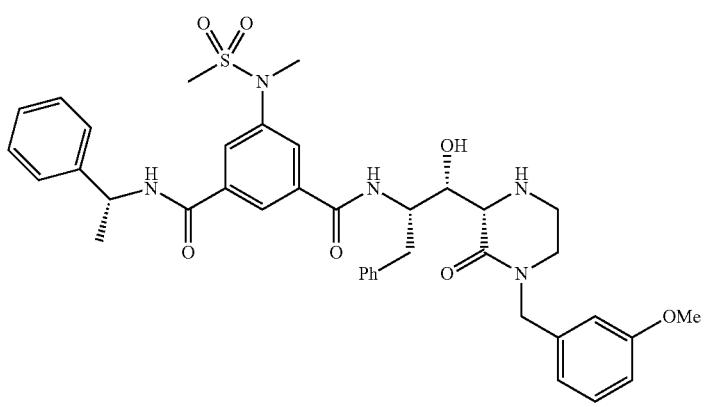 [SMILES: COc1cccc(CN2CCN[C@@H]([C@@H](O)[C@H](Cc3ccccc3)NC(=O)c3cc(C(=O)N[C@H](C)c4ccccc4)cc(N(C)S(C)(=O)=O)c3)C2=O)c1] | 727.87 | <1 μM | NT |

TABLE 1-continued

| Example | Structure | MW | Activity K$_i$ | Activity IC$_{50}$ |
|---------|-----------|-----|----------------|---------------------|
| GRL-0196-AL | 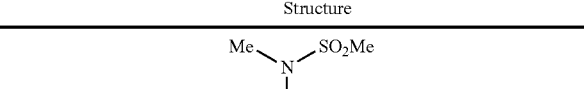 | 640.79 | >10 μM | NT |

Tg2576 Transgenic Mouse model. The compounds described herein are injected intraperitoneally into Tg2576 mice (Hsiao, K.; et al., Science 1996, 274, 99) and the plasma is sampled immediately prior to and 3 h post-administration. Treatment with the compounds described herein may result in a reduction of Ab40 in plasma, such as at 3 h after a single administration. Doses range from about 0.01 mg/kg to about 100 mg/kg, from about 0.1 mg/kg to about 100 mg/kg, from about 0.1 mg/kg to about 10 mg/kg, from about 1 mg/kg to about 100 mg/kg, or from about 1 mg/kg to about 10 mg/kg. Without being bound by theory, it is believed herein that some of the decrease may likely originate from the reduction of Ab in the brain since Ab in young Tg2576 mice is almost entirely produced in the brain (Kawarabayashi, T., et al., Neurosci. 2001, 21, 372) and then transferred to the plasma. Also, the plasma Ab has been shown to correlate well with brain Ab in memapsin 2 inhibition using Tg2576 mice (Chang, W. P., et al., Neurochem., 2004, 89, 1409; Chang, W. P., et al., FASEB J. 2007, 21, 3184). The disclosure of each of the foregoing publications is incorporated herein by reference in its entirety.

I claim:

1. A compound of the formula (III)

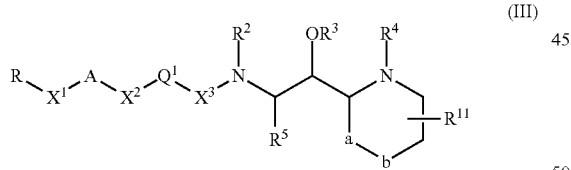

(III)

or a pharmaceutically acceptable salt thereof; wherein
a is optionally substituted methylene or C(O), and b is O, S(O), S(O)$_2$, or NR$^6$;
Q$^1$ is a divalent carbocycle, heterocycle, unsaturated heterocycle, aryl, or heteroaryl, each of which is optionally substituted;
X$^2$ is NR$^1$, C(O), S(O), S(O)$_2$, NR$^1$—C(O), NR$^1$—S(O), NR$^1$—S(O)$_2$, optionally substituted alkylene, or optionally substituted alkylenoxy;
X$^3$ is C(O), S(O), S(O)$_2$ or CHR$^1$;
R is heteroaryl, aryl, heteroarylalkyl or arylalkyl, each of which is optionally substituted;
X$^1$ is optionally substituted alkylene;
A is O or NR$^1$; or A is a nitrogen atom, and A and X$^1$ are taken together to form an optionally substituted heterocycle;

R$^1$ is independently selected in each instance from hydrogen, alkyl, heteroalkyl, cycloalkyl, heterocycloalkyl, aryl, arylalkyl, heteroaryl, or heteroarylalkyl, each of which is optionally substituted;
R$^2$, R$^3$, and R$^4$ are in each instance hydrogen;
R$^5$ is alkyl, alkenyl, heteroalkyl, cycloalkyl, heterocycloalkyl, aryl, arylalkyl, heteroaryl, or heteroarylalkyl, each of which is optionally substituted;
R$^6$ is hydrogen, OR$^7$, S(O)R$^7$, S(O)$_2$R$^7$, C(O)R$^8$, C(O)OR$^7$, C(O)NR$^9$R$^{10}$, S(O)NR$^9$R$^{10}$, S(O)$_2$NR$^9$R$^{10}$, alkyl, alkenyl, heteroalkyl, cycloalkyl, heterocycloalkyl, aryl, arylalkyl, heteroaryl, or heteroarylalkyl, each of which is optionally substituted;
R$^7$ is in each instance independently selected from the group consisting of alkyl, alkenyl, heteroalkyl, cycloalkyl, heterocycloalkyl, aryl, arylalkyl, heteroaryl, and heteroarylalkyl, each of which is optionally substituted;
R$^8$ is in each instance independently selected from hydrogen, or selected from the group consisting of alkyl, alkenyl, heteroalkyl, cycloalkyl, heterocycloalkyl, aryl, arylalkyl, heteroaryl, and heteroarylalkyl, each of which is optionally substituted;
R$^9$ and R$^{10}$ are in each instance independently selected from hydrogen, or selected from the group consisting of alkyl, alkenyl, heteroalkyl, cycloalkyl, heterocycloalkyl, aryl, arylalkyl, heteroaryl, alkylsulfonyl, arylsulfonyl, and heteroarylalkyl, each of which is optionally substituted; or R$^9$ and R$^{10}$ and the attached nitrogen form an optionally substituted heterocycle; and
R$^{11}$ is hydrogen, or R$^{11}$ is alkyl, alkenyl, heteroalkyl, alkoxyl, thioalkyl, haloalkyl, cycloalkyl, heterocycloalkyl, aryl, arylalkyl, heteroaryl, or heteroarylalkyl, each of which is optionally substituted.

2. The compound of claim 1 wherein a is C(O), b is NR$^6$, and R$^6$ is arylalkyl or alkyl.

3. The compound of claim 1 of formula (IIIa) or formula (IIIb)

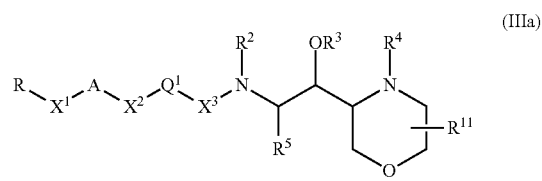

(IIIa)

-continued

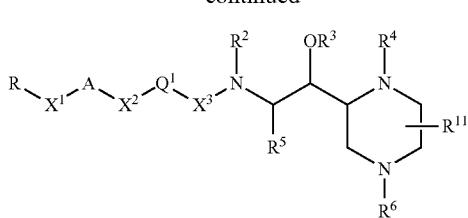
(IIIb)

or a pharmaceutically acceptable salt thereof.

4. The compound of claim 1 of formula (IIIc)

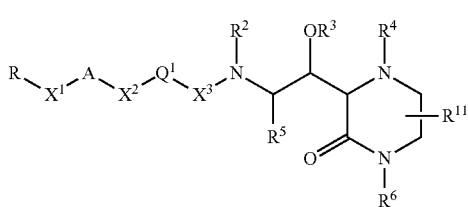
(IIIc)

or a pharmaceutically acceptable salt thereof.

5. The compound of claim 1 of formula (IIIf)

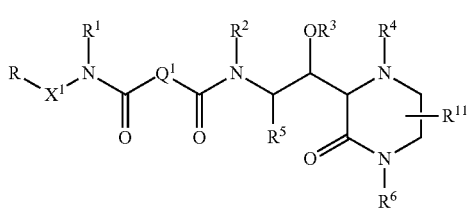
(IIIf)

or a pharmaceutically acceptable salt thereof.

6. A pharmaceutical composition where the pharmaceutical composition includes one or more compounds of claim 1.

7. The compound of claim 1 of formula (IIId) or formula (IIIe)

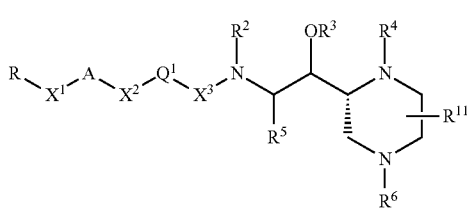
(IIId)

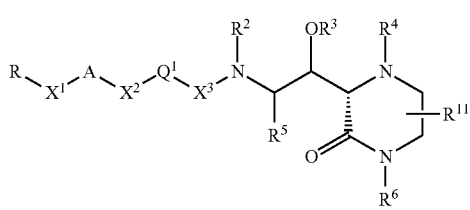
(IIIe)

or a pharmaceutically acceptable salt thereof.

8. The compound of claim 1 wherein $R^6$ is optionally substituted benzyl.

9. The compound of claim 1 wherein $R^6$ is optionally substituted benzyl, and $R^{11}$ is H.

10. The compound of claim 1 wherein $R^6$ is optionally substituted benzyl, and $R^{11}$ is alkyl.

11. The compound of claim 1 wherein $R^6$ is optionally substituted alkyl, and $R^{11}$ is H.

12. The compound of claim 1 wherein $R^6$ is optionally substituted alkyl, and $R^{11}$ is alkyl.

13. The compound of claim 1 wherein $R^6$ is optionally substituted branched alkyl, and $R^{11}$ is H.

14. The compound of claim 1 wherein $Q^1$ is 1,3-phenylene, optionally substituted with from 1 to 3 substituents selected from hydroxy, halo, alkoxy, C(O)-alkyl, C(O)-aryl, C(O)-alkoxy, C(O)-amino, S(O)-alkyl, S(O)$_2$-alkyl, S(O)-aryl, S(O)$_2$-aryl, alkyl, heteroalkyl, cycloalkyl, alkenyl, amino, alkylene-amino, aryl, arylalkyl, heteroaryl, and heteroarylalkyl, each of which is optionally substituted.

15. The compound of claim 1 wherein $X^2$-$Q^1$-$X^3$ is selected from the formulae

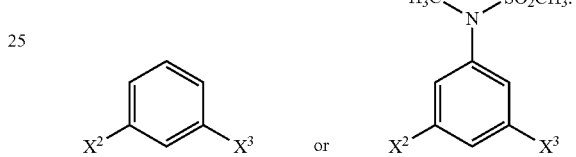

16. The compound of claim 1 wherein $Q^1$ is divalent phenyl optionally substituted with a heteroaryl, selected from the group consisting of pyrrolyl, furanyl, thienyl, pyrazolyl, imidazlyl, oxazolyl, thiazolyl, isoxazolyl, isothiazolyl, pyridinyl, pyridazinyl, pyrimidinyl, and pyrazinyl, each of which is optionally substituted.

17. The compound of claim 1 wherein $Q^1$ is divalent phenyl optionally substituted with a heterocyclyl selected from the group of tetrahydrofuranyl, bistetrahydrofuranyl, tetrahydropyranyl, morpholinyl, piperdinyl, and piperazinyl, each of which is optionally substituted.

18. The compound of claim 1 wherein $X^2$ is C(O).

19. The compound of claim 1 wherein $R^5$ is optionally substituted benzyl.

20. The compound of claim 1 wherein A is a nitrogen atom, and A and $X^1$ are taken together to form an optionally substituted heterocycle.

21. The compound of claim 1 wherein A is NH or N-alkyl, and $X^1$—R are taken together to form

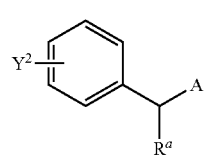

wherein $Y^2$ and $R^a$ are each independently selected from alkyl or heteroalkyl, each of which is optionally substituted.

22. The compound of claim 1 wherein A is NH or N-alkyl, and $X^1$—R are taken together to form a radical of the formula

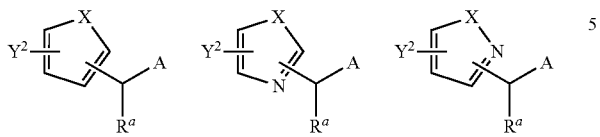

wherein X is $NR^1$, O, or S; and $Y^2$ and $R^a$ are each independently selected from H, or alkyl, haloalkyl, aminoalkyl, or heteroalkyl, each of which is optionally substituted.

23. The compound of claim 1 wherein R—$X^1$-A-$X^2$ are taken together to form a radical of the formula:

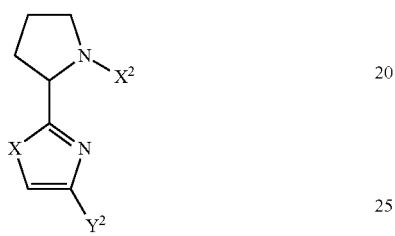

wherein X is O or S; $Y^2$ is hydrogen or halogen, or is alkyl, halo alkyl and heteroalkyl, each of which is optionally substituted.

* * * * *